(12) United States Patent
Toyoda et al.

(10) Patent No.: US 7,164,991 B1
(45) Date of Patent: Jan. 16, 2007

(54) SPECIFIC IDENTIFIERS OF AMINO-ACID BASE SEQUENCES

(75) Inventors: Tetsuro Toyoda, Tokyo (JP); Akiko Itai, Tokyo (JP)

(73) Assignee: Institute of Medicinal Molecular Design Inc., Tokyo (JP)

( * ) Notice: Subject to any disclaimer, the term of this patent is extended or adjusted under 35 U.S.C. 154(b) by 278 days.

(21) Appl. No.: 10/048,479

(22) PCT Filed: Aug. 11, 2000

(86) PCT No.: PCT/JP00/05406

§ 371 (c)(1),
(2), (4) Date: Jun. 11, 2002

(87) PCT Pub. No.: WO01/13268

PCT Pub. Date: Feb. 22, 2001

(30) Foreign Application Priority Data

| | | |
|---|---|---|
| Aug. 11, 1999 | (JP) | 11/227438 |
| Oct. 7, 1999 | (JP) | 11/287020 |
| Nov. 22, 1999 | (JP) | 11/331683 |
| Mar. 7, 2000 | (JP) | 2000-061630 |
| May 19, 2000 | (JP) | 2000-148339 |
| Jul. 26, 2000 | (JP) | 2000-225080 |

(51) Int. Cl.
*G06F 17/00* (2006.01)
(52) U.S. Cl. .......................... 702/19; 702/20
(58) Field of Classification Search .................. 702/19, 702/20
See application file for complete search history.

(56) References Cited

U.S. PATENT DOCUMENTS

| | | | | |
|---|---|---|---|---|
| 5,598,350 A | * | 1/1997 | Kawanishi et al. | ............ 702/20 |
| 5,802,525 A | | 9/1998 | Rigoutsos | ............... 707/103 R |

FOREIGN PATENT DOCUMENTS

WO 98152129 11/1998

OTHER PUBLICATIONS

ENTREZ User's Guide, Release 24.0, Aug. 15, 1996, National Library of Medicine, Bethesda MD.*
T. Coffey et al., "Realisation of a minum-knowledge identification and signature scheme", Computers & Security, vol. 17, No. 3, pp. 253-264 (1994).
Gregory D. Schuler, "Electronics PCR: Bridging the Gap Between Genome Mapping and Genome Sequencing", TIBTECH, vol. 16, pp. 456-459 (1998).

* cited by examiner

*Primary Examiner*—James Martinell
(74) *Attorney, Agent, or Firm*—Greenblum & Bernstein, P.L.C.

(57) ABSTRACT

In order to assign specific identifiers to amino-acid sequences and base sequences, specific identifiers of sequences are generated from data representing connection order of residues in the sequences by using a conversion function, such as collision intractable hash function or universal one-way hash function, and are assigned to the sequences.

19 Claims, 13 Drawing Sheets

Relations among "sequence," "strings of characters representing the sequence" and "the specific identifier of the sequence"

Relations among data records and database

Examples of data records containing sequences

Examples of association of specific identifiers with data records

Procedures of generating specific identifiers to sequences

Application of the specific identifiers in independent databases

Fig. 7

Example of specific identifiers of genotypes, alleles and groups

> Strings of characters representing segments in sequences
>
> Segment1  ATACGTAGTGATGCTGAGTCGCGTAGAGTC...
> (SEQ ID NO: 10)
> Segment2  TGACGTAGCTGACGTCGACGTCGACTGCT...
> (SEQ ID NO: 11)
> Segment3  CGCTGAGTCGATCGTCGACTGACGCTGA...
> (SEQ ID NO: 12)

① Specific identifier of a jointed sequence of above segments

DP1kdoeks9r3mnidosiuwpo32i9dbvsdwe2

② Specific identifiers of above segments

Specific identifier to the segment1: SA1ldoepgiusndkflorkfjgiosfnimirels

Specific identifier to the segment2: SA1k93kdjfiw3mndlspqiuisioonji9d032

Specific identifier to the segment3: SA1si29jiflwifioskopwidninfionsiflw

③ Sorted identifiers of above ② in ascending order

SA1k93kdjfiw3mndlspqiuisioonji9d032

SA1ldoepgiusndkflorkfjgiosfnimirels

SA1si29jiflwifioskopwidninfionsiflw

④ Specific identifier of a group, converted from a jointed string of identifiers of above ③ by using a hash function.

GP1kdoeks9r3mnidosiuwpo32i9dbvsdwe2

Browsing system of data records in multiple databases

Relations of "client's device," "relational information servers" and "private database"

Flow chart of process in "relational information server"

Flow chart of process in "client's device"

Data records managed by local identifiers and searched by specific identifiers of sequences as a query

Data browser automatically generating specific identifiers from data records loaded in the browser, searching databases and displaying the searched results for the user

SPECIFIC IDENTIFIERS OF AMINO-ACID BASE SEQUENCES

FIELD OF INVENTION

This invention relates to assigning method of specific identifiers to amino-acid sequences and base sequences.

BACKGROUND ART

Recently, enormous number of nucleic-acid sequences (herein, referred to as "base sequences") and amino-acid sequences of proteins is known, therefore, database preparations are carried out throughout the world. In most cases, for the newly discovered sequences, identifiers consisting of 6 to 10 alphabets and figures are assigned, and stored in databases together with strings of characters representing the sequences. However, since there are many cases in which identifiers irrelevant to sequences are routinely or arbitrarily assigned to the sequences by analysts and database-preparing organizations, it often happens that different identifiers are assigned to the same sequence and the same identifiers are assigned to different sequences. Accordingly, for the purpose of judging whether or not the same sequence or information related to the same sequence exists in a database, the conventional identifiers cannot be reliably used, and it is necessary to compare several hundreds to thousands of residues for each of known huge number of sequences in a database.

Base sequences and amino-acid sequences are equal information to chemical formulae which specifies structures of substances such as DNA, RNA, peptide and proteins (FIG. 1 ①). Sequences are, in general, information on kinds and connection orders of bases or amino-acids (herein, referred to as "residues" comprised in those substances. Generally, one sequence specifies one substance, however, there are cases in which a sequence specifies multiple substances, for example, a residue "purine" meaning either adenine or guanine can be used for specification of kinds of residues.

A base sequence (or an amino-acid sequence) is usually represented by a string of characters. Usually, each residue is represented by a one-letter or three-letter character as an description unit. However, depending on the notation, the same sequence can be represented by different strings of characters. A string of characters arranged in the connection order of the residues represent the sequence. Herein, a string of characters representing a sequence is "data representing connection order of residues in the sequence" which is one of possible representations of the order of residues in the sequence. For example, an amino-acid sequence in which alanine, leucine and glycine are connected in the order can be represented by "AlaLeuGly" in three-letter notation as shown in FIG. 1 ②, or can be represented by "ALG" in one-letter notation as shown in FIG. 1 ③. These strings of characters are different representations (different in terms of data items) of the same sequence.

In organisms, there exist huge kinds of substances which can be specified by base sequences and amino-acid sequences. Strings of characters representing sequences and information related to the sequences are stored in databases.

If a substance is available, it is possible to determine a connection order of residues by using analytical instruments like sequencers, consequently, a base sequences or an amino-acid sequences is determined and represented as a string of characters representing the sequences, regardless of analysts and analytical sites. Identicalness of sequences can be judged by comparing strings of characters transformed to standard representations. Usually, strings of characters representing sequences are included in data records in databases. Whether different data records contain the same sequence or not is finally judged by the comparison of the standard representation of the sequences in the data records.

Data records containing sequences are available to anyone via the internet from GenBank, EMBL, DDBJ, SWISS-PROT and others. And many published patents and documents contain sequences. In the data record, in addition to strings of characters representing sequences, information related to the sequences, such as original organisms of the sequences, definition of segments within the sequences and features of the segments are filed, where a "file" means a form of data record. Identifiers which must be assigned to sequences uniquely are prone to be used as identifiers assigned to the entire information in the files. This is due to the lack of procedure to assign specific identifiers to sequences. Herein, "unique" means one-to-one correspondence. "Specific identifiers" are unique and consistent identifiers. "Consistent" means that identifiers of the same sequence must be same among all databases. It is always easy to assign unique identifiers to sequences in each database independently, but it is difficult to assign the same identifier to the same sequence in all databases.

It is often the case that different data records are found to contain the same sequence. For example, only information related to the same sequence, such as the original organisms from which the sequence was found, is different among the data records. Biologically, this means that the same sequence was found from different organisms, therefore, the difference of the information are contained in the different data records on purpose. However, since either one of identifiers assigned to the data records is often arbitrarily used as the identifier of the sequence, specific identifiers of sequences are necessary.

There are many data records to which identifiers of clones are assigned. For example, identifiers of clones of cDNA library from which base sequences were found are assigned to the data records containing the base sequences. It is often the case that a base sequence was redetermined from the clone. In this case, the former sequence recorded in the data record would be revised to the redetermined sequence which is often different from the former. That is, before and after the revision of data records, sequences corresponding to the same identifier are altered. Since this kind of revision is often performed, it is troublesome to use those identifiers as reference keys used for describing the information related to the sequence. "Reference key" means a name or a key which specifies the sequence. Specific identifiers play the same role as reference keys under ordinary circumstances. Therefore, specific identifiers of sequences are necessary.

Since assigning methods of identifiers differ from database to database, it is not possible to judge the identicalness of sequences or segment/segments of sequences based only on the comparison of their identifiers only. Therefore, the only ways to judge whether sequences contained in data records among different databases are the same or not are either to compare strings of characters representing the sequences or to depend on link information indicating relations among identical sequences. Considering the fact that more data records containing sequences will be registered in independent databases in the future, it is desirable to establish a method of generating identifiers based on data which uniquely specify the sequences and to used it uniformly in all databases to maintain the consistency of identifiers among all databases.

DISCLOSURE OF THE INVENTION

An object of the present invention is to provide a method of assigning substantially specific identifiers to amino-acid sequences or base sequences based on data representing connection order of residues in the sequences. To be more clearly, the object of the present invention is to provide a method of generating the same identifier for the same sequence and substantially different identifiers for different sequences based on data representing connection order of residues in the sequences, and generating the same identifier for the same segment/segments of sequences and substantially different identifiers for different segment/segments of sequences based on data representing connection order of residues in the segment/segments of sequences, and assigning the generated identifiers of fixed short length to the sequences of various lengths.

Other object of the present invention is to provide specific identifiers used for description of information related to sequences or segment/segments of sequences, because short identifiers are conveniently used for this purpose rather than prolonged strings of characters representing sequences. Moreover, the object of the present invention is to provide specific identifiers used for description of relations among sequences and/or segment/segments of sequences, because short identifiers are also conveniently used for this purpose rather than prolonged strings of characters representing sequences.

Furthermore, other objects of the present invention are to provide a database-integration method which can be used in many databases uniformly in order to maintain relations and consistency among data records in databases by specific identifiers of sequences, a method of assigning the same identifiers to the same sequences and the same segment/segments of the sequences contained in data records in multiple databases, a method of associating the same identifiers with the data records containing the same sequences and the same segment/segments of sequences, a method of associating the same identifiers with the data records containing information related to the same sequences and the same segment/segments of sequences, a method by which database managers are able to generate globally-consistent identifiers by themselves instead of retrieving global identifiers from authorities such as GenBank, a method of searching data records which contain the same sequence and the same segment/segments of sequence in one or more databases by using the same identifier as a query, and a method which enables to generate specific identifiers at different computers and transmit them among the computers via the internet without causing any inconsistency of the identifiers.

For description of varieties of genome sequences of same and/or different species, it is preferable to divide a whole chromosomal sequence into one or more segments and assign a specific identifier to each segment or group of some of the segments and use the identifiers in the description, rather than strings of characters representing the sequences. For the comparison of varieties of genome sequences, it is more convenient to compare with these short identifiers rather than comparing with the prolonged sequences. For this purpose, other object of the present invention is to provide a generation method of specific identifiers used for these purposes.

Other object of the present invention is to provide specific identifiers used for consistent description of relations among sequences, segment/segments of sequences, genotypes and/or alleles, and to provide specific identifiers used for consistent description of information related to sequences, segment/segments of sequences, genotypes and/or alleles, and to provide specific identifiers used for judgment whether information in different data records are on the same sequence or not, only by comparison of the specific identifiers.

Moreover, other object of the present invention is to provide globally consistent identifiers so that data records containing sequences can be exchanged between remote databases via the internet without care about the name space of the identifiers, and to provide a generation method of globally-consistent specific identifiers used to describe annotations at different web sites so that annotations described at different web sites can be easily integrated and understandably viewed by only comparing the specific identifiers.

As a result of zealous endeavor to solve above-mentioned objects, the inventors succeeded in solving the above-mentioned objects by generating specific identifiers of sequences from data representing connection order of residues in the sequences by using a conversion function including collision intractable hash function and/or universal one-way hash function (FIG. 1 ④), and assigning the identifiers to the sequences.

The present invention thus provides a method of generating specific identifiers to base sequences, amino-acid sequences and segment/segments of sequences, wherein the identifiers consist of characters and figures of fixed or variable length generated by conversion function including one or more kinds of functions from data representing connection order of residues in base sequences or amino-acid sequences.

In the preferred embodiment of the present invention, functions including collision intractable hash function and/or universal one-way hash function is used as the conversion function, more preferably, a function including SHA (Secure Hash Algorithm) or SHA1 are used to generate strings of characters and figures as identifiers.

The present invention also provides:

a method of generating the identifiers with further appendage of one or more characters and figures pertaining to additional information on the generation method of the identifiers, characters and figures indicating additional information on the sequences, means of acquisition, the kinds of detection methods, their categories and the like;

a method of assigning the same identifier to the same sequence and the same segment/segments of the sequence among data records of one or more databases, by utilizing the same conversion function for each generation of the identifier by the above-mentioned method;

a method of associating the same identifier with data records containing the same sequence and the same segment/segments of sequences among multiple databases;

a method of associating the same identifier with data records containing the same sequence and the same segment/segments of sequences among multiple databases wherein the data records do not include data representing connection order of residues in the sequence nor the segment/segments of the sequences;

a method of searching data records containing sequences or segment/segments of sequences or genotypes or alleles by utilizing above-mentioned identifiers;

a method of search and/or management of documents or electronic files including experiment records, clinical trial records, medical records, attached papers to drugs, application forms, notices, medical certificates, certificates, reports, descriptions of patents, technical literature, archives, summaries, and/or integrated viewing of the group of files;

a method of generating a specific identifier of a data record containing a sequence or segment/segments of a sequence, wherein the identifier is generated based on both the specific identifier of the sequence and all of the data for information related to the sequence in the data record, whereby the generated identifier is substantially specific to the combination of the sequence and information related to the sequence in the data record;

a method of generating a specific identifier of group of multiple sequences and/or segment/segments of sequences, wherein the identifier is generated based only on and all of the specific identifiers of the sequences, whereby the generated identifier is substantially specific to the combination of the sequences and/or segment/segments of sequences in the group;

a method of keeping secrecy of sequences without using information which specifies sequence data easily but using only the aforementioned identifiers for comparison and/or search, and a device for said comparison and/or search; and a method of keeping secrecy of sequences without transmitting the data representing the order of residues in the sequence but transmitting the aforementioned identifiers for comparison and/or search via networks and/or the internet.

From other points of view, there are also provided:

specific identifiers of base sequences or amino-acid sequences generated by the above-mentioned method;

the above-mentioned identifiers used for judgment of the identicalness of sequences and segment/segments of sequences;

the above-mentioned identifiers used as reference keys of sequences and segment/segments of sequences;

the above-mentioned identifiers to search data records containing the same sequence and data records containing the same segment/segments of sequences in one or more databases;

the above-mentioned identifiers used for management of above databases;

the above-mentioned identifiers used as a query or one part of a query for database search;

the above-mentioned identifiers used to describe relations among sequences;

the above-mentioned identifiers used to describe information related to sequences;

the above-mentioned identifiers included in data records containing base sequences converted from measured data by sequencer, mass spectra, or DNA chips;

the above-mentioned specific identifiers of proteins which base sequences or the complementary base sequences code at least in part;

the above-mentioned identifiers used for the storage and communication of information related to the sequences;

the above-mentioned identifiers used for the description of genotypes or alleles of a whole or segment/segments of base sequence among the same and/or different species;

the above-mentioned identifiers used for the comparison of genotypes or alleles of a whole or segment/segments of base sequence among the same and/or different species;

the above-mentioned identifiers used to indicate genotypes or alleles and keep anonymity or secrecy of individuals or samples; the above-mentioned identifiers of genotypes or alleles;

the above-mentioned identifiers of genotypes or alleles of the corresponding base sequences and/or amino-acid sequences obtained from individuals, group of individuals, cell lines, organisms, strains, samples from which extraction of nucleic acids or proteins is possible;

the above-mentioned identifiers to indicate genotypes associated with data records of individuals and groups of individuals as targets of effective treatments including medication and/or ineffective targets and/or the targets in which the differences in effects are recognized;

the above-mentioned identifiers to be included in documents or electronic files including experiment records, clinical trial records, medical records, attached papers to drugs, application forms, notices, medical certificates, certificates, reports, descriptions of patents, technical literature, archives, summaries and the like;

the above-mentioned identifiers used for search and/or management of experiment records, clinical trial records, medical records, attached papers to drugs, application forms, notices, medical certificates, certificates, reports, descriptions of patents, technical literature, archives, summaries, documents or electronic files;

specific identifiers of a data record containing a sequence or segment/segments of a sequence, generated based on both the specific identifier of the sequence and all of the data for information related to the sequence in the data record, and substantially specific to combination of the sequence and information related to the sequence in the data record; and a specific identifier of group of multiple sequences, generated by sorting identifiers of the sequences (for example, ascending order) and jointing them to form a string of characters sequentially composed of the identifiers and converting the string to an identifier of fixed length by a conversion function.

These identifiers may be stored in media such as optical disks, magnetic disks and memories.

There are also provided media recording computer programs implementing the above-mentioned methods; and data records including above-mentioned identifiers in the data records and/or in the names of the data records.

From other points of view, there are provided:

an apparatus utilizing the above-mentioned method and the above-mentioned identifiers; the above-mentioned apparatus which searches data records associated with above-mentioned identifiers;

the above-mentioned apparatus for search and/or management of documents or electronic files including experiment records, clinical trial records, medical records, attached papers to drugs, application forms, notices, medical certificates, certificates, reports, descriptions of patents, technical literature, archives, summaries;

the above-mentioned apparatus, further comprising a browser used to view data records and/or used as a client's device on networks and/or the internet;

the above-mentioned apparatus, further comprising a local database in the client's device;

the above-mentioned apparatus, further comprising one or more databases;

the above-mentioned apparatus, further comprising data-record-service means working on networks and/or the internet;

an integrated viewer of the group of those files;

media recording the computer program to be used for above-mentioned apparatus;

A method of converting above-mentioned identifiers into bar codes, the above-mentioned identifiers to be used as bar codes, or a device for output and/or input of bar codes;

the above-mentioned identifiers in which some characters such as check sum was further added to detect input errors from keyboards and bar codes, and a device to detect input errors using these identifiers;

client's and server devices used for that comparison and/or search; printed matters, files, records, data objects, file names, file pathnames, URLs, anchor tags in which above-mentioned identifiers are included, means to record them, or a device to search those using the identifiers;

a device to input above-mentioned identifiers, a means to read those identifiers, a means to record those identifiers, a device to output those identifiers, and a means to transmit those identifiers;

a program module that utilizes above-mentioned identifiers as the identifiers of substances in simulation of intracellular interactions by computer, the above-mentioned identifiers used for identifiers of program modules which plays roles of substances in simulation, the above-mentioned identifiers used for defining intermolecular interactions in the simulation;

a data browser, or simply, a browser which can directly generate identifiers from strings of characters representing sequences contained in a viewed data record and search other data records associated with the identifiers; and media recording one of the aforementioned identifiers are provided.

"Data record" used herein means a data object, a unit of data for storage, a data object to be searched, a data item, a file, a record in relational databases, an object in object-oriented databases, a node of a document object model, a section enclosed by tags used in markup language such as XML and the like (FIG. 2). "Database" herein used means an apparatus managing one or more data records and is able to serve data records on request, for example, a relational database, an object-oriented database, a file system, a file server, an internet information server. In FIG. 2, information contained in a data record may be strings of characters representing sequences, information related to sequences, identifiers, or additional information appended to the data record. "Data-record-service means" is a database or an apparatus serving information in a form of data record. "Sequence database" means the database in which one part or the whole groups of data records contain sequences and/or segment/segments of sequences. As shown in FIG. 3, "data records containing sequences" are data records including strings of characters representing sequences, data records containing information related to sequences, data records including identifiers of sequences, and data records including identifier of other data records containing sequences. "Segment/segments of sequence" is a segment in a sequence, or a sequence created by jointing segments in a sequence, where each segment is specified by numbers such as orders of residues, indicating the first point and end point of the segment in the sequence (for example, numbers indicating regions seen in the "FEATURES" section of GenBank files). Thus, "segment/segments of sequence" is a sequence, and created from a string of characters representing a sequence and information specifying segment/segments in the sequence.

"Association of an identifier with a data record" means to let the data record accessible by the identifier, searchable by the identifier as a query, or inclusive the identifier. Identifiers may be associated with data records by making correspondence between the identifiers and local identifiers of the data records. "Local identifier" may be "primary keys or reference keys of data records used only in a database" or "path names and file names used only in a file system." For example, when local identifiers were already associated with data records containing sequences (FIG. 4①), the correspondence table of the local identifiers and the specific identifiers (referred to as "EigenIDs" in FIG. 4②) of the sequences and/or data records including "EigenIDs" of the sequences in the original data records are provided as a preferred mode. When there are multiple sequences in data records, their "EigenIDs" of each sequence can be also included in the data records (FIG. 4③) and/or an identifier representing their group (FIG. 4④) is provided. "Assignment of an identifier to a sequence" means to define one-to-one correspondence between the identifier and the sequence.

BRIEF EXPLANATION OF DRAWINGS

FIG. 7 shows examples of identifiers of genotypes, alleles and groups.

BEST MODE FOR CARRYING OUT THE INVENTION

Figure 1:
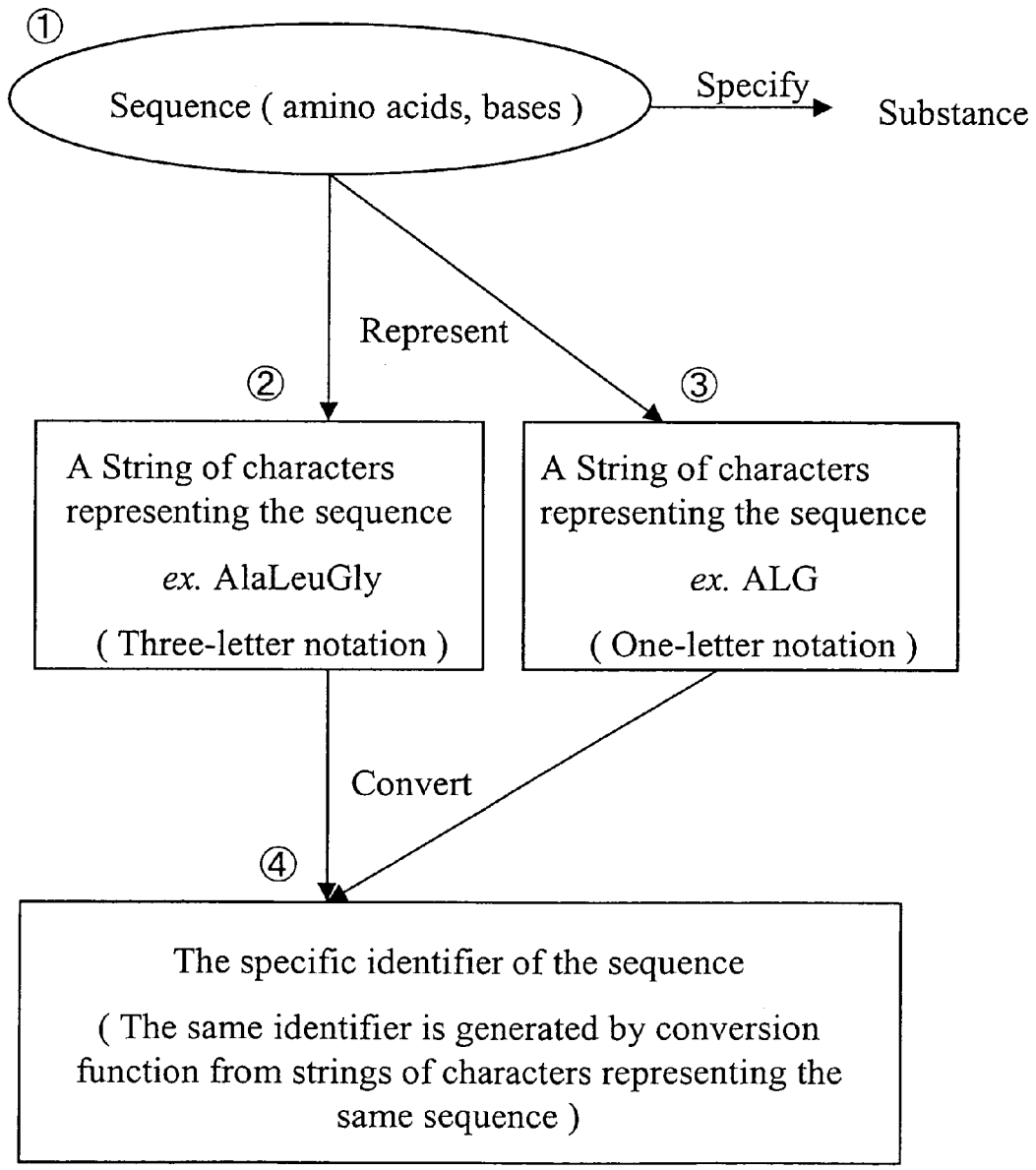
FIG. 1 shows relations among "sequence," "strings of characters representing the sequence" and "the specific identifier of the sequence."
Figure 2:
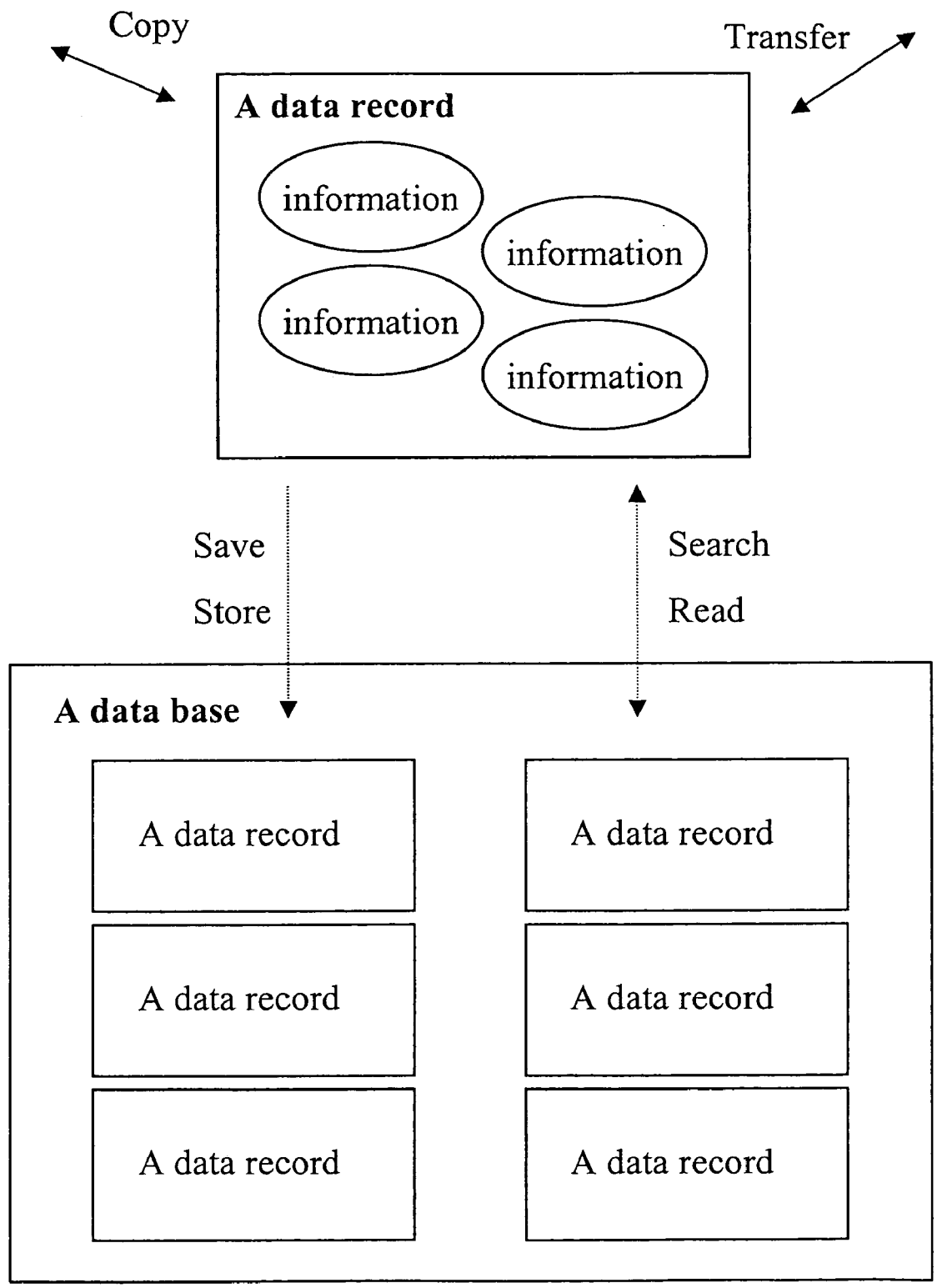
FIG. 2 shows a relation among data records and database.
Figure 3:
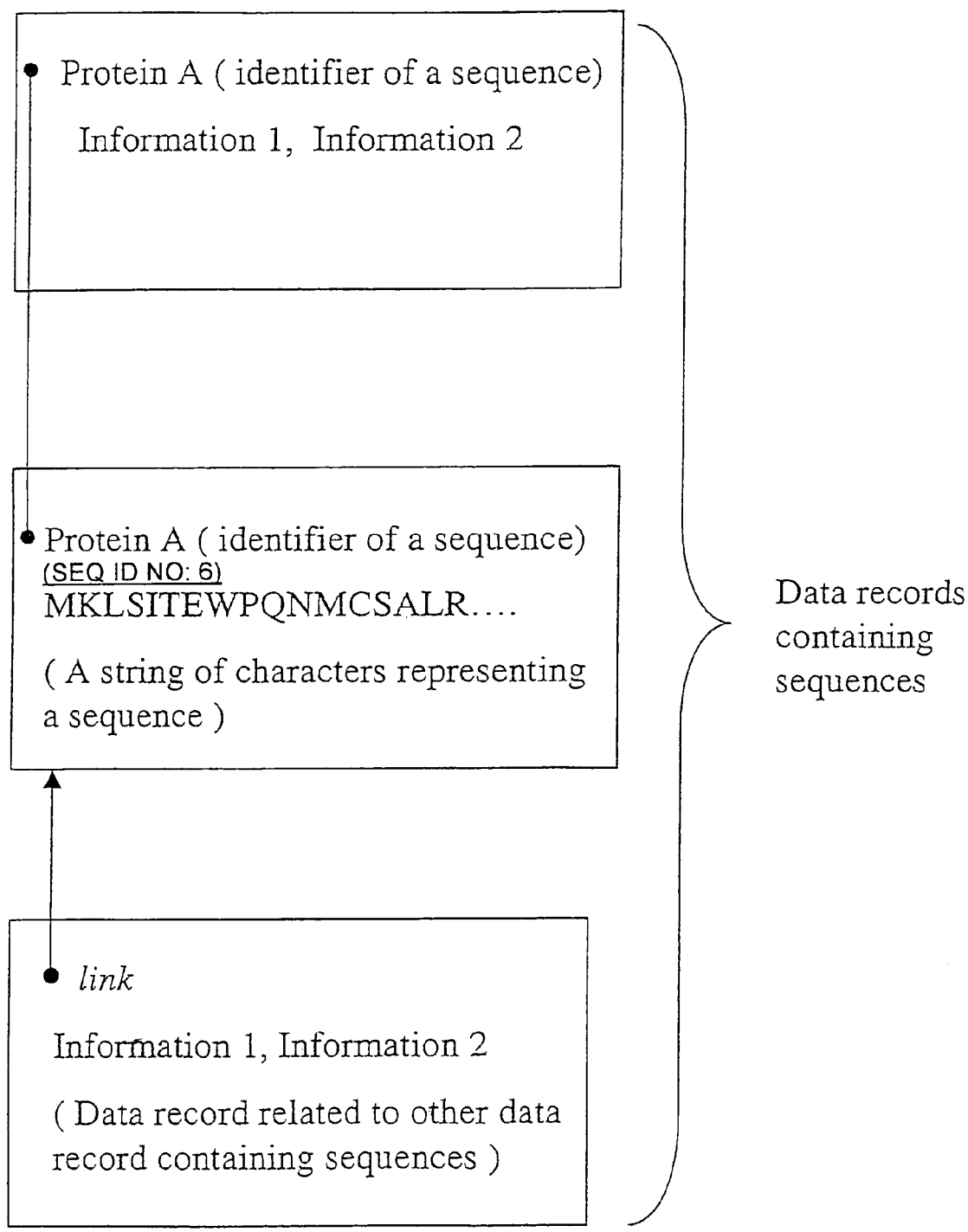
FIG. 3 shows examples of data records containing sequences.
Figure 4:
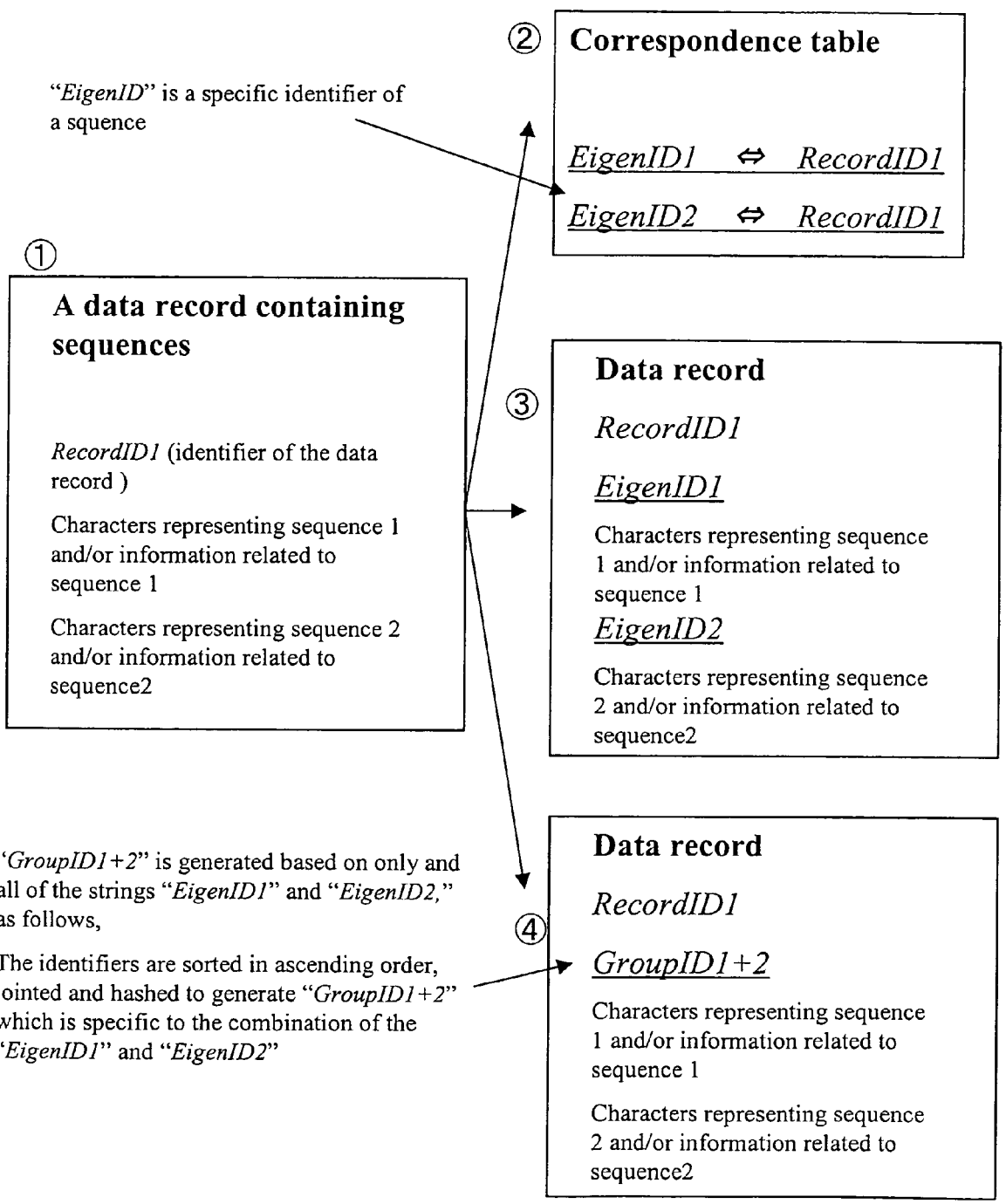
FIG. 4 shows example of association of specific identifiers and data records.

Method of the present invention includes a process of generating identifiers consisting of characters and figures of certain or arbitrary length, preferably certain length by using conversion functions from the data representing connection order of residues in base sequences or amino-acid sequences, which possesses the following characteristics:

(1) The same identifiers are generated from the same sequences.

(2) Possibility of generating the same identifiers from different sequences is extremely low or substantially zero.

(3) Identifiers are generated as a string of characters and figures or a string of bits, preferably a string of alphabets and figures of certain or arbitrary length, preferably certain length.

(4) Generation scheme is simple.

"String of characters and figures" used in this description consist of characters and/or figures used throughout the world such as alphabets, Arabic figures, Chinese characters, Japanese characters, the Hankul, besides these characters and figures, symbols like @, →, ¥, &, $ and any characters expressed by character codes in computers are included. For example, alphabets, characters and figures comprising alphabets and Arabic figures are pointed out as typical examples. Preferably, a string of characters and figures are converted to a string of bits or bytes by computers using a character cord table such as ASCII, UNICODE, etc. There are cases in which they are recorded in a printed form on paper, bar codes and others. Moreover, there are cases in which they are recorded as a bit map expressing characters and figures. Mode of recording is not limited. Furthermore, "conversion function" is an implementation of an algorism to convert input data to output data. Preferably, suitable computer programs are used for the conversion functions.

A conversion function suitably used in the method of the present invention utilizes hash functions, more preferably collision intractable hash function and/or universal one-way hash function are pointed out. However, as conversion functions used in the present invention, collision intractability and one-directionality, preferably collision intractability is not necessarily mathematically proved strictly. Practically, any function which almost satisfies the above-mentioned characteristics as the conversion results may be employed.

Universal one-way hash function was introduced by Noar and Yung, and is a function wherein it is difficult to obtain the value y which satisfies h(x)=h(y) when the function h and a value x in the defined area are given.

On the other hand, collision intractable hash function was introduced by Damgard, and is a function wherein it is difficult to obtain a pair of different values (x,y) which satisfys h(x)=h(y) when the function h is given.

As for the required conditions for the functions, collision intractable hash function is more strict than universal one-way hash function (for hash functions, consult T. Okamoto and H. Yamamoto: "Series/Johokagaku no Sugaku Gendai Ango (Mathematics of Information Science: Modern Cryptograph)" Sangyo Tosho; E. Okamoto: "Ango Riron Nyumon (Introduction to Encription Theory)" Kyoritsu Shuppan as an introduction). In the present description, hash functions particularly collision intractable hash functions or universal one-way hash functions should be interpreted in the broadest sense, and in any sense, they should not be interpreted limitedly. As a means of the present invention, any function classified as collision intractable hash function or universal one-way hash function may be used.

Moreover, while aiming at having collision intractability, many hash functions have been proposed which were developed emphasizing the practical effectiveness. Since MD-4, MD-5 by Rivest and PIPEMD, SHA(secure hash algorithm) which are based on MD-4 and MD-5 are widely used (Menezes, A. J., van Oorschot, P. and Vanstone, S. A.: Handbook of Applied Cryptography, CRC Press, 1996), these functions may be used for the present invention. One or more kinds of different conversion functions, for example, one or more kinds of collision intractable hash functions and one or more kinds of universal one-way hash functions may be combined and used. Furthermore, for instance, one or more kinds of collision intractable functions and one or more kinds of universal one-way hash functions may be properly combined and processed. As a means of the present invention, it is particularly preferable to use SHA or SHA1 solely, however, functions to be used and the combination of functions can be reasonably selected by those who are skilled in the art in order to decrease the collision possibility of identifiers thoroughly.

In the following, the algorithm of SHA used in a conversion function particularly favorably applicable to the present invention is introduced. However, conversion functions applicable to the present invention are not limited to SHA. In this example, the string of characters and figures generated by the treatment of hash functions as hash values are expressed by the combination of small-letter characters of alphabets and figures, but the characters are not limited to the small letters of alphabets. Furthermore, a high speed hash method with higher collision intractability may be used as a substitute for SHA. For example, SHA1 which is an improved model of SHA may be used.

*Input data

Bit string [m] of arbitrary length which is less than 264 bits (a method of converting base or amino acid sequence data to bit string [m] is described later).

*Output data

Hash values of 160 bits are generated to [m].

Padding is conducted as the following procedures in order for the input bit string [m] to be multiple numbers of 512 bits (16×32 bits)

Procedure 1) Bit string of "100 . . . 00" is added to the end of [m] in order for the bit string length of [m] to be '512N−64'.

Rf.) "|m|": the bit string length of [m]
N=(|m|+64)/512

Procedure 2) Bit string length of input sequence is expressed by 64 bits, and further added to the end bit string.

The padded bit string is divided into N blocks of 512 bits each, which forms M1, M2, . . . , Mn.

| $M_1$ | $M_2$ | ... | $M_N$ |

 Each Mi is divided into 16 blocks of 32 bits each.

| $W_0$ | $W_1$ | ... | $W_{15}$ |

To the divided bit string, using the constants and functions explained below, hash values are calculated by the following process.

(Constants) The initial constants are represented as hex values.

H0=67452301
H1=EFCDAB89
H2=98BADCFE
H3=10325476
H4=C3D2E1F0
Kt=5A827999 (0≦t≦19)
Kt=6ED9EBA1 (20≦t≦39)
Kt=8F1BBCDC (40≦t≦59)
Kt=CA62C1D6 (60≦t≦79)

(Functions)

$$ft(x, y, z) = (x \wedge y) \vee (x \wedge z) \quad (0 \leq t \leq 19)$$
$$ft(x, y, z) = x \oplus y \oplus z \quad (20 \leq t \leq 39)$$
$$ft(x, y, z) = (x \wedge y) \vee (x \wedge z) \vee (y \wedge z) \quad (40 \leq t \leq 59)$$
$$ft(x, y, z) = x \oplus y \oplus z \quad (60 \leq t \leq 79)$$

注) ∧ : AND
∨ : OR
⊕ : XOR

* Procedure

The following process is repeated for i equals 0 to N.
(1) Mi is divided into 16 blocks of 32 bits each, which are labeld $W_0, W_1, \ldots, W_{15}$, where $W_0$ is the left-most block.
(2) $W_t=(W_{t-3} \oplus W_{t-8} \oplus W_{t-14} \oplus W_{t-16})<<<1$ determines $W_{16}, \ldots, W_{79}$ (32 bits each)
  rf.4) "X<<<n" means a rotation shift of bit string of X by n bits to the left.
    Rotation Shift: bit string is slided by one bit in certain direction, and
    the character ad one end is moved to the opposite end.

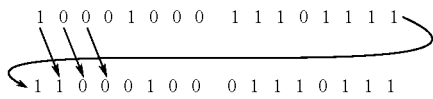

(3) The variables A, B, C, D, E are initialized as follows.
  A=H0, B=H1, C=H2, D=H3, E=H4
(4) The following steps is repeated for t equals 0 to 79. rf.5)
  '+' indicates the remainder which is obtained by the division of the sum of the values on the left side and right side by "$2^{32}$".
  TEMP=(A<<<5)+ft (B, C, D)+E+$W_t$+Kt
  E=D
  D=C
  C=B<<<30
  B=A
  A=TEMP
(5) H0=H0+A, H1=H1+B, H2=H2+C, H3=H3+D, H4=H4+E The total of 160 bits combined by the bitstring of H0~H4 finally obtained become hash values.

Figure 5:
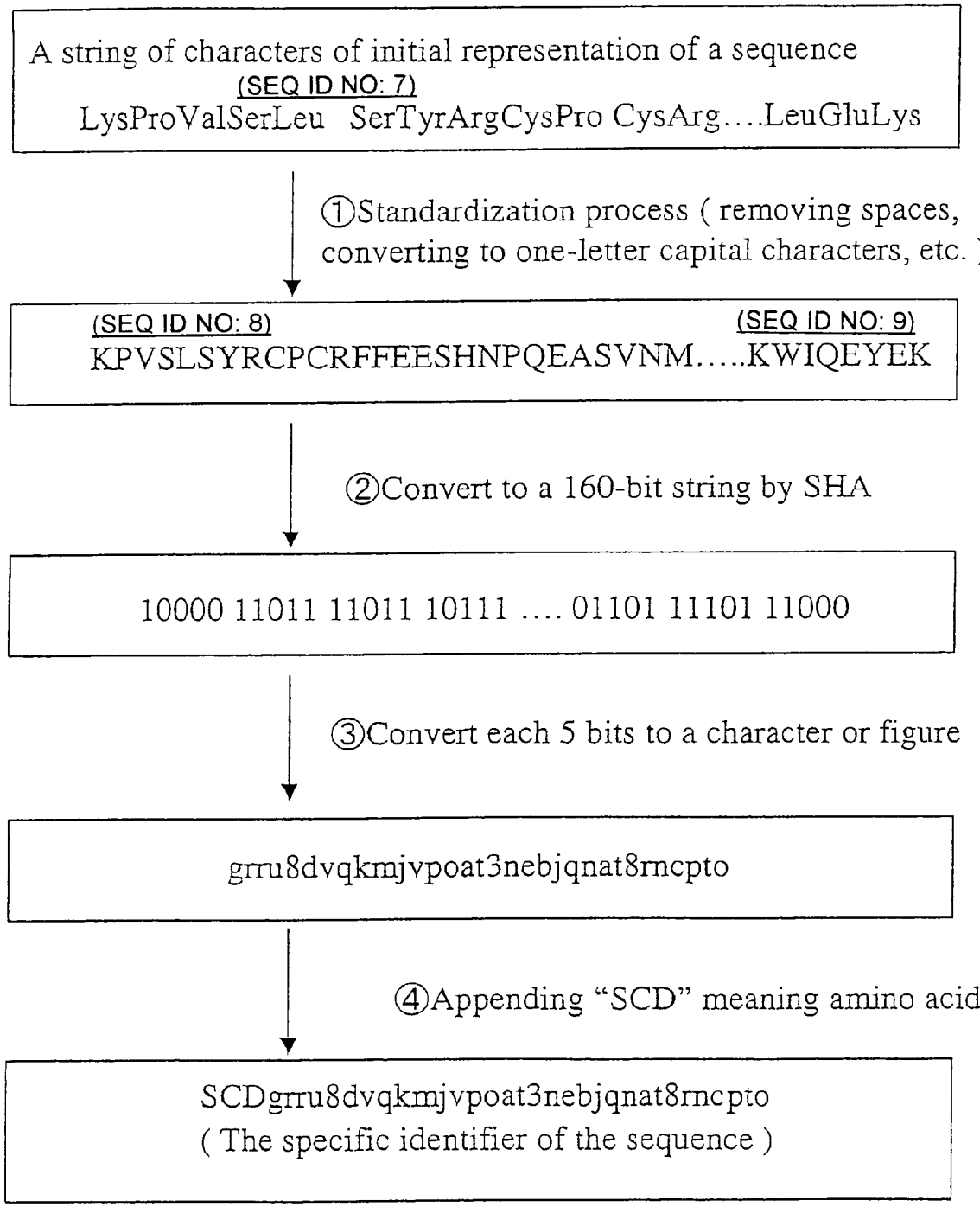
FIG. 5 shows procedures of generating specific identifier of sequences.

Data used for the input to conversion function is referred to as "an initial representation of a sequence." The procedure of converting the initial representation of a base sequences or amino-acid sequence to the bit string [m] which is input data for above-mentioned SHA is explained in the following. In an initial representation, characters representing residues in the sequence may be expressed in various notations. "Standardization process" transfers an initial representation to a "standard representation" in which characters of residues and their order in the sequence are uniquely represented. For example, a base sequence is represented by a string of characters (for example A, T, G, C) representing each nucleic acid by a one-letter character and is arranged in the order, and for amino-acid sequences, similarly a string of characters in which each amino acid is represented by a one-letter character and arranged in the order, is used. Small-letter characters are converted to capital-letter characters. "Arranged in the order" means the removal of characters (such as spaces, hyphens) irrelevant to nucleic acids and amino acids and the process of putting the characters representing each residue in the order as the same connection order of each residue in the sequence. Thus, the string of characters representing the sequences is standardized (FIG. 5 ①). Subsequently, the process in FIG. 5 ② is conducted. Since one character can be converted by ASCII code to 8 bit information, a bit string which are composed of each 8 bits arranged in the order of characters is created. This procedure is employed in the example of present description, however, when the characters are converted to a bit string, conversion code other than ASCII code may be used. Thus, an initial representation of the same sequence is converted to the same bit string regardless of the notation of the initial representation of the sequence. Then, the bit string is converted to 160-bit string by SHA. Hereupon, "bit string" means a series of arranged 1 bit information. One bit corresponds to 1 place of binary numbers and is expressed by 0 or 1. When ASCII code is used, the condition of SHA which is less than 264 bits means about less than $2 \times 10^{18}$ characters, which is a enough length to express actual base sequences and amino-acid sequences.

In order to utilize the 160-bit string (obtained as the result of FIG. 5 ② procedure) obtained by the above-mentioned hash functions as an identifier, the bit string are divided into necessary bits so that the bit string can be represented by alphabets and figures. 160 bits are divided to 5 bits, and each 5 bits are represented by corresponding one of 32 characters, 0, 1, 2, 3, 4, 5, 6, 7, 8, 9, a, b, c, d, e, f, g, h, i, j, k, l, m, n, o, p, q, r, s, t, u, v" (FIG. 5 ③).

The following 160-bit string is divided by 5 bits each, and converted to corresponding 32 characters.

The 160-bit string is divided by 5 bits, and 5-bit string is converted into an integer or a character.

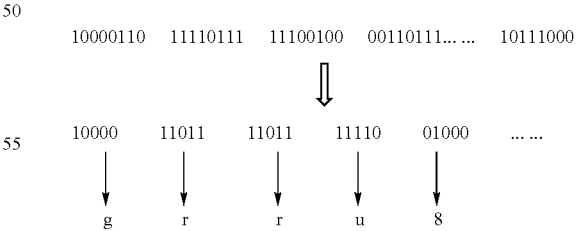

Finally, we get following string as an identifier.
"g r r u 8 d v q k m j v p o a t 3 n e b j q n a t 8 r n c p t o"

As shown in above, string of characters and figures of "grru8dvqkmjvpoat3nebjqnat8rncpto" are obtained as hash values.

For the identifiers generated by a method of the present invention, in order to add information indicating the kind of corresponding sequence (for example, information indicating that the identifiers is of sequences, information distinguishing amino-acid sequences or base sequences, the number and location of chromosomes in which base sequences are found, species, location of SNP) and information indicating the kind of generating procedure of identifiers (for example, information indicating the kind of conversion functions used), one or more characters and figures of fixed lengths, preferably alphabets and figures may be further appended to above-mentioned hash values to form new identifiers (FIG. 5 ④). The appended characters and figures may be placed in any part, for example, may be placed to the head or to the tail of the string of characters and figures obtained as above-mentioned hash values. Preferably, three or less characters and/or figures are appended to the head of the hash values.

Moreover, the procedure of the present invention may be applied to the whole length or segment/segments of a sequence. For example, by applying only to the open reading frames or exons in a base sequences, it is possible to generate the identifier assignable to the segment/segments coding a protein, or it is possible to generate the identifier of the coded protein. In the latter case, a process of translation to an amino-acid sequence from the open reading frames using codon table is necessary.

Figure 6:
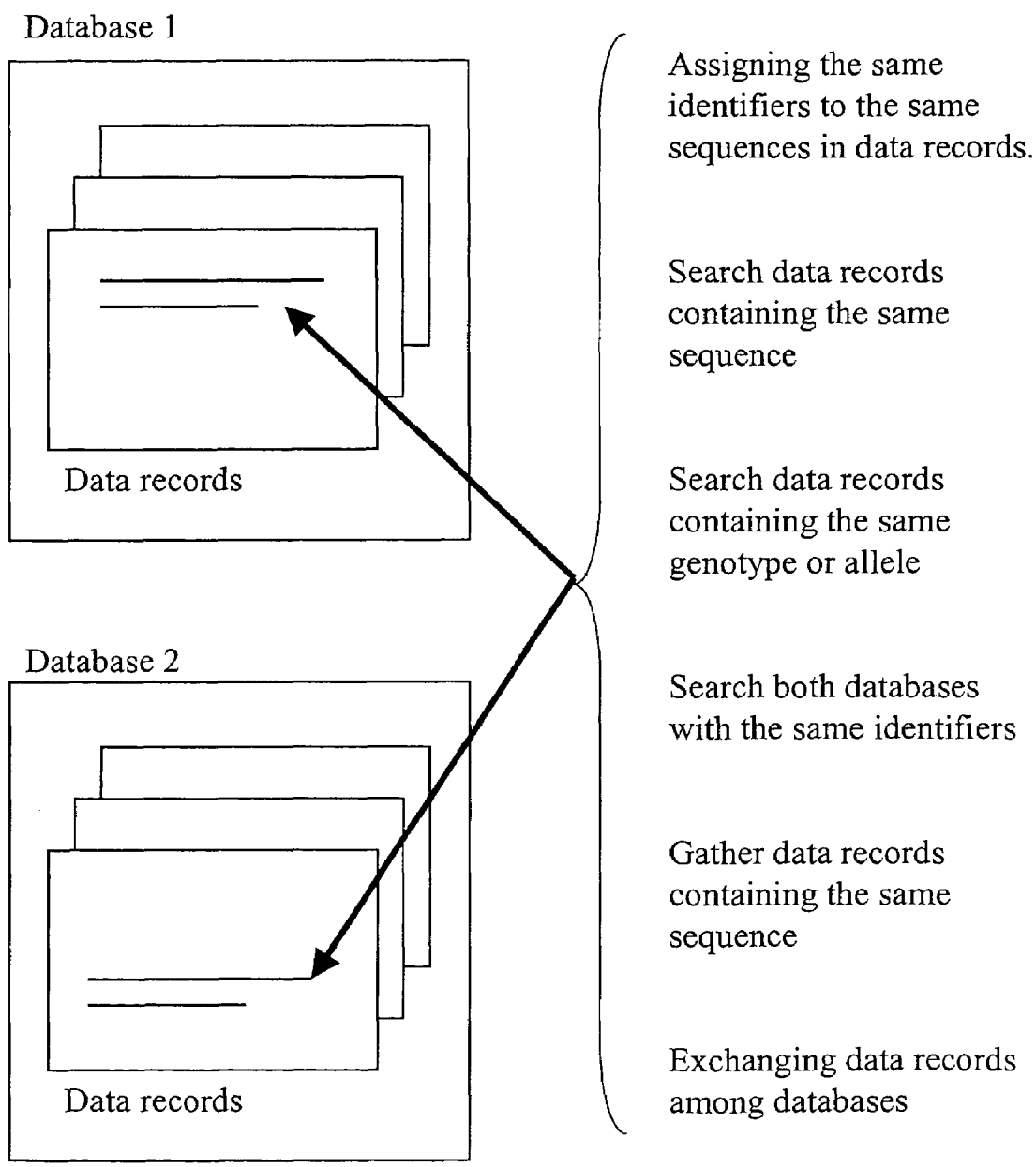
FIG. 6 shows applications of the specific identifiers in independent databases.

Identifiers of the present invention can be applied to management and comparison of base sequences and/or amino-acid sequences. Moreover, the identifiers can be used for management of information related to sequences (FIG. 6). Since above-mentioned identifiers are specific to each sequence and the possibility of collision is very low, by generating identifiers from strings of characters representing sequences using a procedure of the present invention, it is possible to judge the identicalness of sequences easily and speedily by comparison of their identifiers. For example, by using the above-mentioned identifiers, it is possible to search the same sequences contained in data records in multiple sequence databases. Furthermore, by using above-mentioned identifiers in sequence databases, it is possible to detect overlapping sequences in sequence databases, or detect the same sequence redundantly registered in different databases easily and quickly. Moreover, when a new data record containing sequences is registered in a database, it is possible to judge easily whether the sequences has been already registered or not. For the above-mentioned purpose, suitably relational databases, object-oriented databases or file systems, more suitably relational databases, are applicable. And above-mentioned identifiers are suitably used as primary keys or unique reference keys of the sequence contained in data records in the relational databases. Furthermore, for the comparison of sequences, only identifiers are necessary to be released. It is possible to preserve the confidentiality of sequences without releasing data representing connection order of the sequences. Furthermore, by using above-mentioned identifiers, it is possible to construct and maintain sequence database easily. For example, above-mentioned identifiers can be used to describe relations among sequences, describe information related to sequences, search data records by above-mentioned specific identifiers of sequences contained in the data records, manage databases by associating above-mentioned identifiers with data records.

Furthermore, since the above-mentioned methods are applicable to multiple databases uniformly, it is possible to integrate the databases by above-mentioned globally-consistent identifiers. If they are used uniformly among multiple databases, it is feasible to maintain relations and consistency by assigning the same identifier to the same sequences contained in data records among databases. Moreover, for purpose of describing one part or the whole genome, the entire base sequences of chromosomes of genome are divided to one or more segments, it becomes possible to describe the divided segment/segments represented by short identifiers. By comparing these identifiers, easy comparison of varieties among the same and/or different species becomes possible rather than comparison of prolonged sequences. Furthermore, above-mentioned identifiers can be used for purpose of describing relations among sequences. For example, for the execution of "Describing and Storing Method of Alignment Information" (Japanese Patent Request No. (Hei) 11-15189 Description), it is effective to use them as specific identifiers of sequences.

Moreover, identifiers of the present invention can be used to indicate genotypes and alleles. A genotype is description of one of varieties of the whole or a segment or a group of segments of base sequences of genome of the same species and/or different species, and is a symbol reflecting the identicalness of the segments of the base sequences. As genotypes of individuals, group of individuals, cell lines, organisms, species, samples in which nucleic acids or proteins are extractable, those identifiers generated from data representing connection order of residues in a segment of the base sequences or a group of segments of the base sequences can be used.

A specific identifier of a jointed sequence of the whole and/or a segment and/or segments of sequences in a certain order (FIG. 7①) may be used as an identifier of a genotype, an allele or a group. A group of identifiers of each segment of sequences (FIG. 7②) may be used as identifiers of genotypes. Furthermore, (FIG. 7④) a string of characters and figures of fixed length generated by a conversion function from a string of characters formed by jointing of those identifiers in ascending order or descending order (FIG. 7③) may be used as an identifier of a genotype, an allele or a group. Moreover, identifiers appended with characters and/or figures of one or more characters indicating additional information on the genotype, allele or group may be used.

They may be used as identifiers to indicate genotypes of individuals and groups of individuals, as targets of effective treatments including medication and/or ineffective targets and/or the targets in which difference in effects are recognized. By using above-mentioned identifiers as genotypes, it is possible to keep anonymity and secrecy of individuals and samples and describe information related to the genotype. In the documents including experiment records, clinical trial records, medical records, attached papers to drugs, application forms, notices, medical certificates, certificates, reports, descriptions of patents, technical literature, archives, summaries, they can be used for the purpose of genotype description.

EXAMPLES

The present invention will be explained more specifically by way of examples. However, methods of the present invention are not limited to the following examples.

Example 1

Data records containing amino-acid sequences of hemoglobins of human, whale and rat are as follows.

Data record 1:

>Human (SEQ ID NO:1)

1 GLSDGEWQLVLNVWGKVEADIPGHGQEV-
LIRLFKGHPETLEKFDKFKHLK

51 SEDEMKASEDLKKHGATVLTALG-
GILKKKGHHEAEIKPLAQSHATKHKIP

101 VKYLEFISECIIQVLQSKHPGDFGADAQ-
GAMNKALELFRKDMASNYKELG

151 FQG

Data record 2:

>Whale (SEQ ID NO:2)

1 VLSDAEWQLVLNIWAKVEADVAGHGQDI-
LIRLFKGHPETLEKFDKFKHLK

51 TEAEMKASEDLKKHGNTVLTALG-
GILKKKGHHEAELKPLAQSHATKHKIP

101 IKYLEFISDAIIHVLHSRHPGDFGADA-
QAAMNKALELFRKDIAAKYKELG

151 FQG

Data Record 3:

>Rat (SEQ ID NO:3)

1 GLSDGEWQLVLNVWGKVEGDLAGHGQEV-
LIKLFKNHPETLEKFDKFKHLK

51 SEDEMKGSEDLKKHGNTVLTALG-
GILKKKGQHAAEIQPLAQSHATKHKIP

101 IKYLEFISEAIIQVLQSKHPGDFGADAQ-
GAMSKALELFRNDIAAKYKELG

151 FQG

Standard representations (represented by one-letter characters) of each sequence from above data records are as follows.

Standard representation of sequence of human hemoglobin:

GLSDGEWQLVLNVWGKVEADIPGHGQEV-
LIRLFKGHPETLEKFDKFKHLKSEDEMKAS
EDLKKHGATVLTALGGILKKKGHHE-
AEIKPLAQSHATKHKIPVKYLEFISECIIQVLQSKHP
GDFGADAQGAMNKALELFRKDMASNYKELGFQG
(SEQ ID NO: 1)

Standard representation of sequence of whale hemoglobin:

VLSDAEWQLVLNIWAKVEADVAGHGQDI-
LIRLFKGHPETLEKFDKFKHLKTEAEMKASE
DLKKHGNTVLTALGGILKKKGHHEAELK-
PLAQSHATKHKIPIKYLEFISDAIIHVLHSRHP GDF-
GADAQAAMNKALELFRKDIAAKYKELGFQG (SEQ
ID NO: 2)

Standard representation of sequence of rat hemoglobin:

GLSDGEWQLVLNVWGKVEGDLAGHGQEV-
LIKLFKNHPETLEKFDKFKHLKSEDEMKG
SEDLKKHGNTVLTALGGILKKKGQH-
MEIQPLAQSHATKHKIPIKYLEFISEAIIQVLQSKH
PGDFGADAQGAMSKALELFRNDIMKYKELGFQG
(SEQ ID NO: 3)

Identifiers were generated by application of a method of the present invention to above amino-acid sequences. Herein, conversion function includes SHA. Identifiers are the following.

Human hemoglobin:

agtiu9e70upqugdqp895bgesc3ops288

Whale hemoglobin:

c21tv2116bjcuj1crtd6r23tm984n74i

Rat hemoglobin:

1582i4737s9vkd4cd8mfcug8rq19cqal

In addition to above three amino-acid sequences, the inventors generated identifiers for over 60,000 unique amino-acid sequences in SWISS-PROT and 4,700,000 unique base sequences in DDBJ (all the data available in 1999), and found that no collision of identifiers was occurred.

Example 2

To the head of the above identifiers, [CDJ] meaning that they are "amino-acid" sequences are added.

Human hemoglobin:

SCDagtiu9e70upqugdqp895bgesc3ops288

Whale hemoglobin:

SCDc21tv2116bjcuj1crtd6r23tm984n74i

Rat hemoglobin:

SCD1582i4737s9vkd4cd8mfcug8rq19cqal

Example 3

Two identifiers were obtained using two kinds of hash functions for the same sequences as in Example 1. Combination of these identifiers has a characteristic of extremely lower probability of collision than identifiers in Example 1. For the above-mentioned sequence of human, hash values of "agtiu9e70upqugdqp895bgesc3ops288"

and

"cd8mfcug8rq19cqalcd8mfcug8rq19a1"

were obtained by application of two of the hash functions. And these were combined to generate "agtiu9e70upqugdqp895bgesc3ops288cd8mfcug8rq19cqalc
d8mfcug8r q19a1"

as an identifier of the present invention.

Example 4

The following identifier was generated by adding a character "L" indicating the application of two of above hash functions and characters "SCD" indicating amino-acid sequences to the head.

"LSCDagtiu9e70upqugdqp895bgesc3ops288cd8mfcug8rq1
9cqalcd8mfc ug8rq19a1"

Comparing this identifier with

"SCDagtiu9e70upqugdqp895bgesc3ops288"

which was generated by one kind of hash function, it tells difference of the generating procedures at the head of the characters, furthermore, it tells that this identifier is "amino-acid" sequences.

Example 5

There are three files (herein, corresponding to data records) as shown in the following based on the XML (Extensible Markup Language) format which is one of formats used for describing data in text form.

The contents of file 1 are following two lines.

<sequence id="SA1c7isymyeju52cep94q8f01p4vd5y37fu">EDLQGD AVPETSATKDDNE XPEMIPM</sequence> and

<sequence id="SA1gptg04a3tskj0s8u604h0cme86yqiufd">DDLQGTA VQERSAKASDEE EAIRTLL</sequence>

The contents of file 2 are following one line.

<name id="SA1c7isymyeju52cep94q8f01p4vd5y37fu">ProteinA</name>

The contents of file 3 are following one line.

<name id="SAlgptg04a3tskj0s8u604h0cme86yqiufd">ProteinB</name>

In XML, a string of characters which exist from "<" to ">" is called a tag. In file 1, the string of characters between <sequence> and </sequence> means a string of characters representing a sequence. Id="-----" inserted in the <sequence> tag indicates an assignment of the specific identifier to the amino-acid sequence represented by the characters between the tags. That is, the identifier assigned to the amino-acid sequence represented by the string of characters "EDLQGDAVPETSATKDDNEXPEMIPM" (SEQ ID NO: 4) is "SA1c7isymyeju52cep94q8f01p4vd5y37fu," and the identifiers to the amino-acid sequence represented by the string of characters "DDLQGTAVQERSAKASDEEEAIRTLL" (SEQ ID NO:5) is "SA1gptg04a3tskj0s8u604h0cme86yqiufd."

In files 2 and 3, the characters between <name>and </name> are a name of a sequence. Id=inserted in the <name> tag is a reference key (herein, the identifier is associated with the section from <name> to </name>) for the amino-acid sequence to which the name in the tag corresponds. That is, information in file2 means that the specific identifier of the amino-acid sequence to which the name "ProteinA" corresponds is "SA1c7isymyeju52cep94q8f01p4vd5y37fu," and information in file 3 means that the specific identifier of the amino-acid sequence to which the name "ProteinB" corresponds is "SA1gptg04a3tskj0s8u604h0cme86yqiufd."

Figure 8:
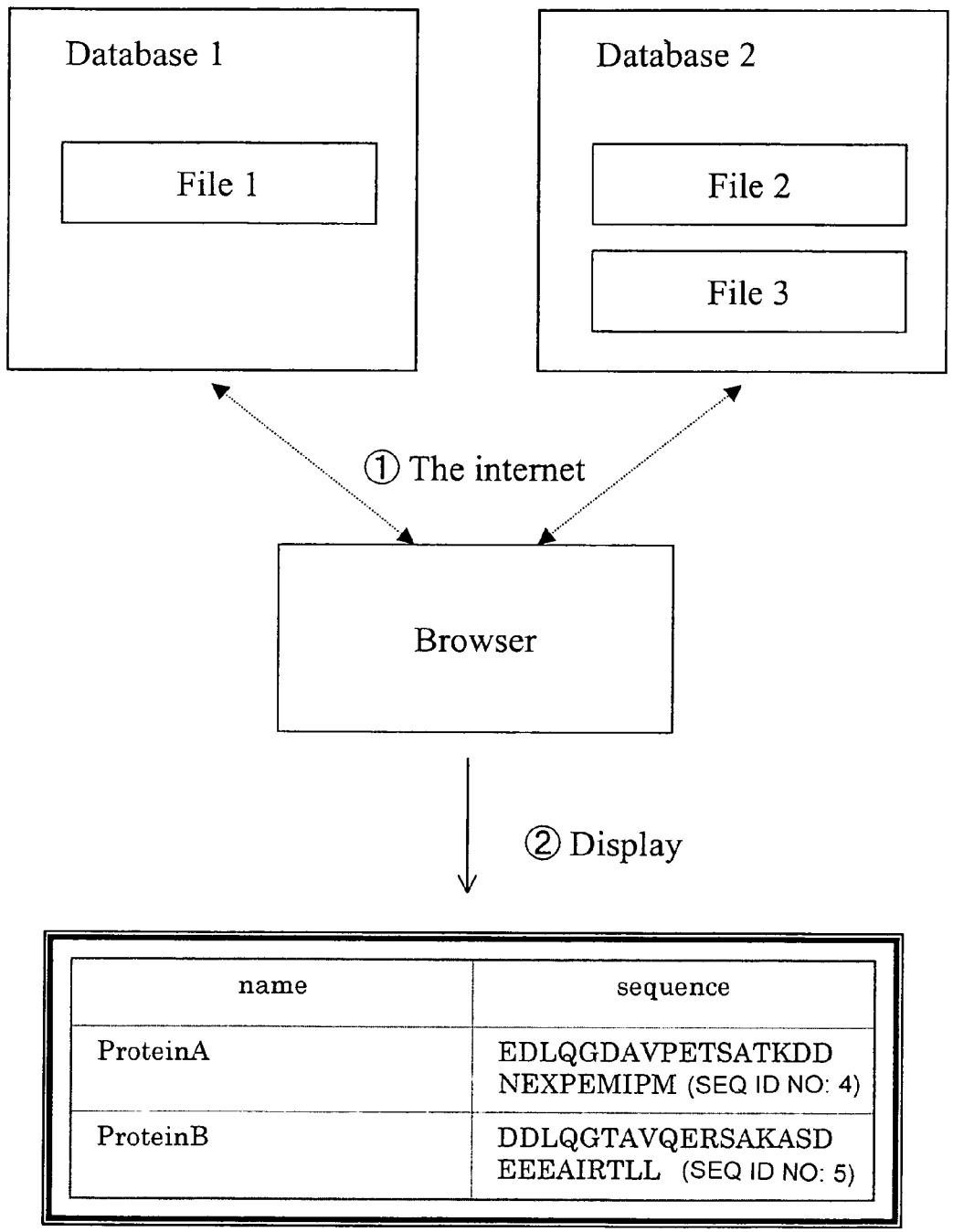
FIG. 8 shows an example of browsing system of data records in multiple databases.

As shown in FIG. 8, file 1 exists in database 1, and file 2 and file 3 exist in database 2. For database search, a browser can be utilized. When the browser loads a file including specific identifiers from a database, the browser is so made as to search automatically files with which the identifiers are associated in the other database using the identifiers as a query and loads the searched files on it. Database land database 2 and the browser can be located in the same computer or separated computers connected via networks or the internet (FIG. 8①).

When a search was performed using a string of characters "ProteinA" as a query to database 2 from the browser, file 2 was obtained as the search result. Since the specific identifier "SA1c7isymyeju52cep94q8f01p4vd5y37fu"of a sequence was included in the file 2, the browser automatically searched database 1 with the identifier. As a result, file 1 was loaded as the search result. Since a specific identifier "SA1gptg04a3tskj0s8u604h0cme86yqiufd" of another sequence was found in file 1, the browser successively searched database 2 using the identifier as a query. Consequently, file 3 was loaded as the search result. As the result of above, file 1, file 2, and file 3 were loaded on the browser.

Then, the browser gathered up and displayed information related to the same sequence by following algorithm.

(1) In those files, identifiers marked by id="- - - - - - -" included in tags were compared among the tags. Characters enclosed by the tag containing the same identifier is judged as information on the same sequence.

(2), Information on the same sequence is placed in the same rows and tag names are placed in the head of the columns, all information is displayed in a form of a table.

As the result of above, a table shown in FIG. 8② was displayed by the browser. Number of databases in this system is not limited only two, and can be more than two.

Example 6

There is a data record containing a sequence. The specific identifier of the sequence is "SA1c7isymyeju52cep94q8f01p4vd5y37fu".

The identifier of the record is

"AA1001."

A dictionary object associating both identifiers are constructed as follows using programming language "VBScript."

Set dictionary=CreateObject("Scripting.Dictionary") dictionary.Add "SA1c7isymyeju52cep94q8f01p4vd5y37fu", "AA1001"

Example 7

Figure 9:
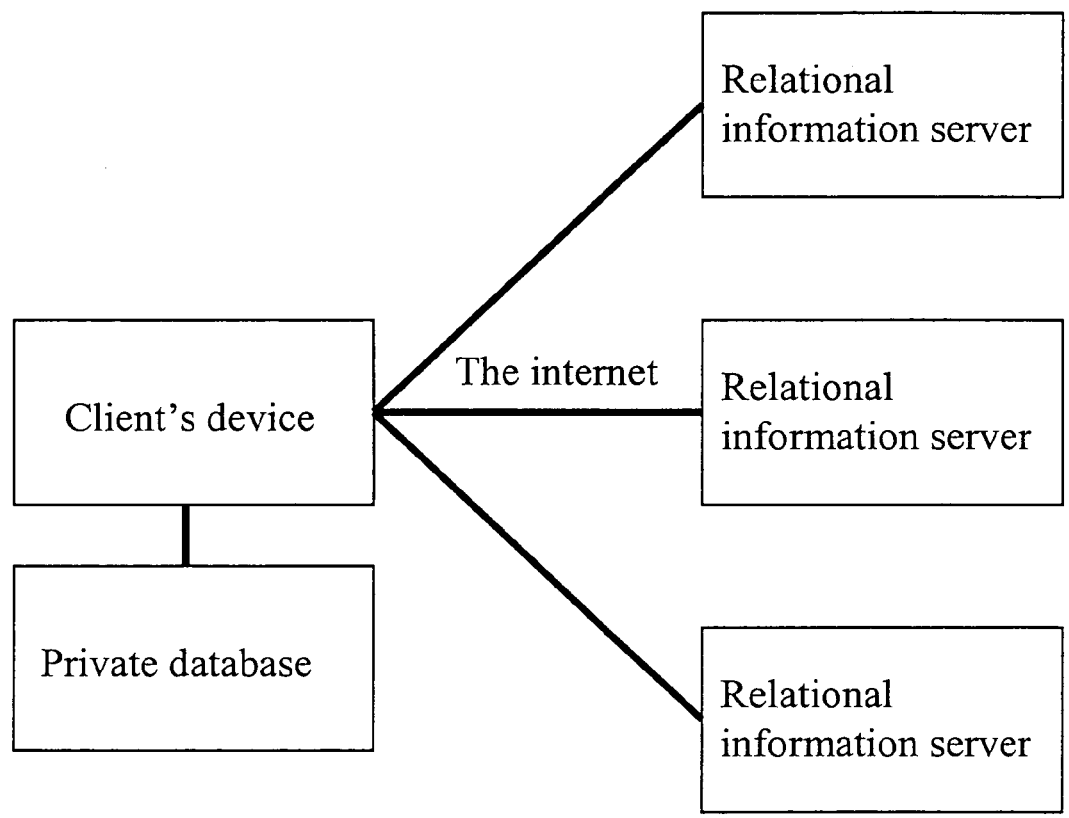
FIG. 9 shows an example of relations of "client's device," "relational information servers" and "private database."

Even though entire sequences of human genome have been sequenced, functions of most of genes remain unknown. Therefore, for base sequences coding genes and amino-acid sequences of proteins which are translated products of the genes, various predictions and experiment results are added as related information. Herein, information related to sequences is referred to as "annotation." A business model of "annotation-service providers" is explained. In order to provide annotations on prediction of gene functions, a system shown in FIG. 9 was constructed. In FIG. 9, "client's device" is a device which a client who wants to obtain information related to a certain sequence uses for that purpose, a string of characters representing the sequence is transmitted by ciphers to one or more "relational information servers" through the internet. The "relational information server" generates annotations to the sequence by predicting functions of the received sequence and/or by searching in databases, and sends back the generated annotations to the client by return files. "Client's device" displays the annotations contained in the returned files to the client. "Client's device" is connected to a private database in which annotations in returned files have been accumulated. If annotations in a newly returned file do not exist in the private database, "Client's device" informs the client that the annotations are new at the time of view. One or more "relational information server" exists in the system. A "relational information server" is a data-record-service means in the system.

Figure 10:
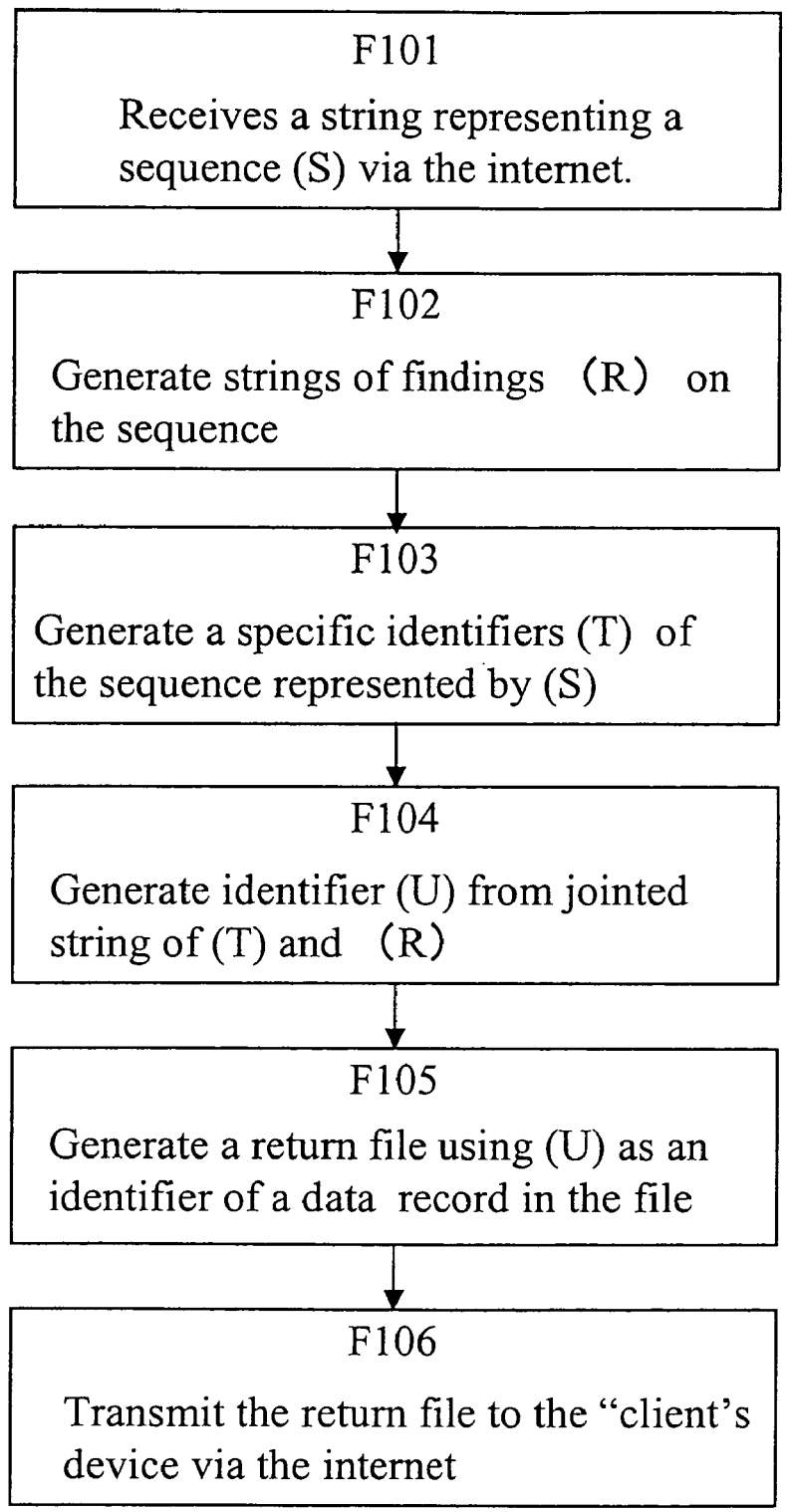
FIG. 10 is a flow chart of process in the "relational information server."
Figure 11:
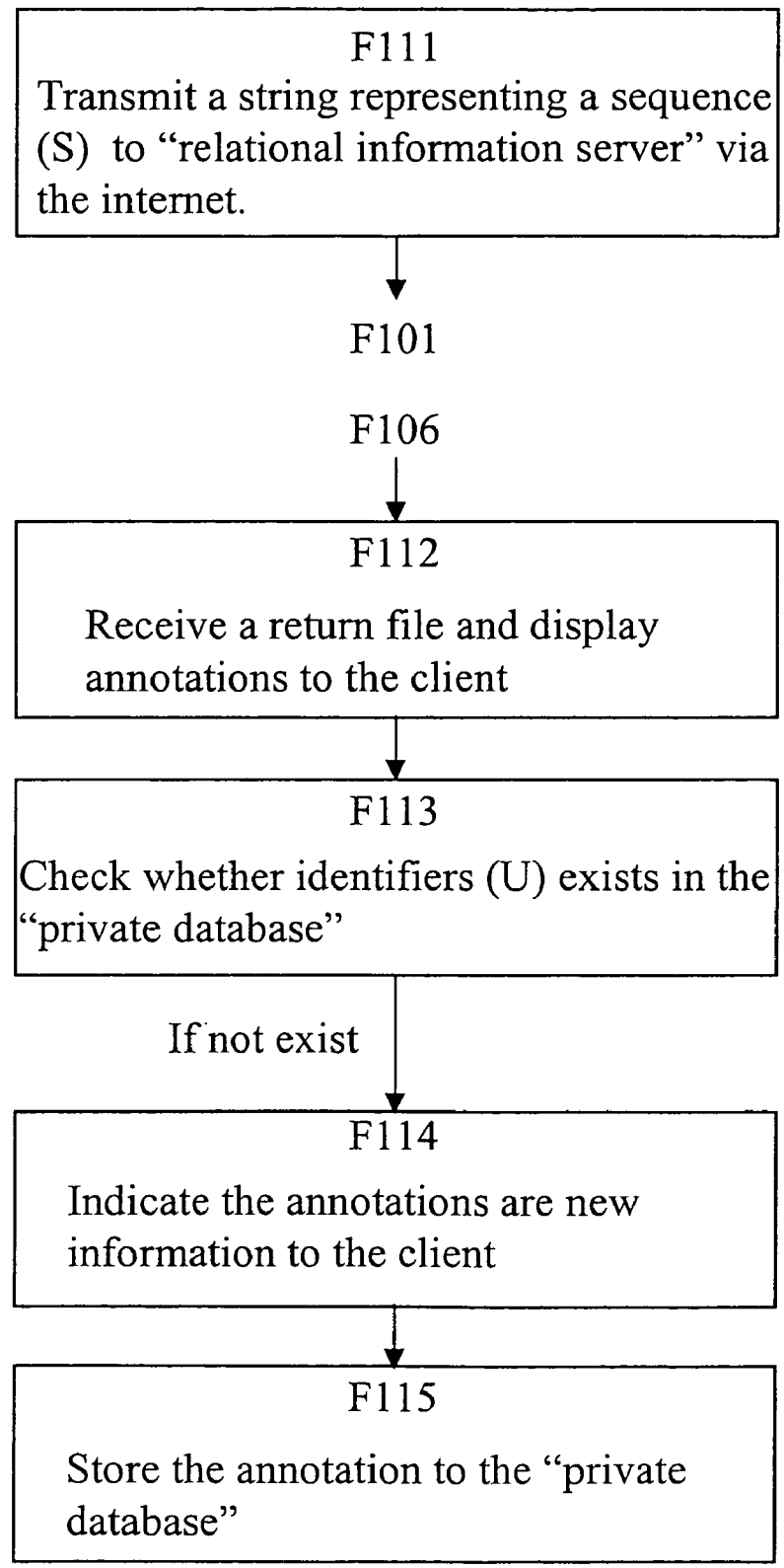
FIG. 11 is a flow chart of process in the "client's device."

In this example, "Client's device" transmits a string of characters representing a sequence(S) via the internet to "relational information servers" (FIG. 11-F111). In this case, the string of characters (S) is "EDLQGDAVPETSATKDD-NEXPEMIPM." (SEQ ID NO: 4) When the "relational information server" receives the string of characters (S) (FIG. 10-F101), it starts regular search programs and/or prediction programs such as prediction of functions of the sequence and/or searching databases. Consequently, information related to the sequences is generated (FIG. 10-F102). The result is expressed in a string of characters referred to as "findings" on the sequence. In this case, the following two findings (R1),(R2) was generated.

"Signal Peptide" (R1)

"Listed on Literature X" (R2)

From the string of characters (S) representing the sequence, identifiers (T) for the sequence were generated by a method of the present invention (FIG. 10-F103).

"SA1c7isymyeju52cep94q8f01p4vd5y37fu." (T)

Then, two strings of characters were generated by jointing (T) and each of findings (R1), (R2) as shown in FIG. 10-F104.

"SA1c7isymyeju52cep94q8f01p4vd5y37fuSignal Peptide" (T-R1)

"SA1c7isymyeju52cep94q8f01p4vd5y37fuListed on Literature X" (T-R2)

These strings of characters are specific to the combination of the specific identifier (T) of the sequence (S) and each of the strings of characters of the finding (R1) and (R2) Therefore, strings converted from above strings of characters (T-R1) and (T-R2) by a collision intractable hash function become substantially specific identifiers to the combination of the sequence and the findings. The generated identifiers (U1), (U2) to (T-R1) and (T-R2) in this way are "d92fe7v6qfdqnihh8prdg7b73f75b56u" (U1)

"1bdr3kabuhbnghvx5arp8xe8uas22xqc" (U2)

The results were stored in a return file in XML format as follows;

<RESULT id="d92fe7v6qfdqnihh8prdg7b73f75b56u">

<SEQUENCE id="1bdr3kabuhbnghvx5arp8xe8uas22xqc"/>

<INFORMATION> Signal Peptide</INFORMATION>

</RESULT>

<RESULT id="1bdr3kabuhbnghvx5arp8xe8uas22xqc">

<SEQUENCE id="SA1c7isymyeju52cep94q8f01p4vd5y37fu"/>

<INFORMATION> Listed on Literature X</INFORMATION>

</RESULT>

Similarly, an identifier of a data record (herein, each of sections enclosed by <RESULT> and </RESULT>) is generated based on both the sequence's identifier and all of the data related to the sequence (herein, characters between <INFORMATION> and </INFORMATION>) in the data record, thus, the generated identifier is substantially specific to the combination of the sequence and the data related to the sequence in the data record. A return file may be generated using (U) as an identifier of a data record in the file. (FIG. 10-F105.) "All of the data related to a sequence" may be composed of multiple sections, depending on the format of the data record.

However, in this invention, order of storing strings of characters of (R1), (R2), (T), (U1), and (U2) into a return file is not limited to this example. And further information such as string of characters (S) may be stored. The format is not limited to above-mentioned formats.

This return file is transmitted to "client's device" via the internet (FIG. 10-F106). "Client's device" receives this file (FIG. 11-F112) and displays the annotations to the client. Furthermore, it judges whether or not the identifiers (U1) and (U2) included in each <RESULT> tag exist in the "private database." (FIG. 11-F113.) If they don't exist, "client's device" indicates that it is novel information to the client. (FIG. 11-F114.) And the annotation are stored in the "private database." (FIG. 11-F115.)

Moreover, it is possible to judge whether or not the same annotation exists in files returned from several "relational information servers" by comparing the identicalness of the identifiers.

Furthermore, in the "client's device," it is possible to display all of the annotations related to the same sequence by judging the identicalness of sequences to which annotations are related, by comparing their specific identifiers in each file transmitted from independent "relational information servers" and "private database." In order to give understandable presentation of the gathered files for the client, the "client's device" shows them in a form of a table by arranging information related to the same sequence in the same columns or rows. Owing to the generation method of identifiers in present invention, even though the identifiers for sequences are generated in independent "relational information servers," it is possible to assign the same identifiers to the same sequence, therefore, this feature is an essential function for the above-mentioned business model. In the returned file in this example, identifiers of sequences are used for description of information related to the sequences.

Example 8

Figure 12:
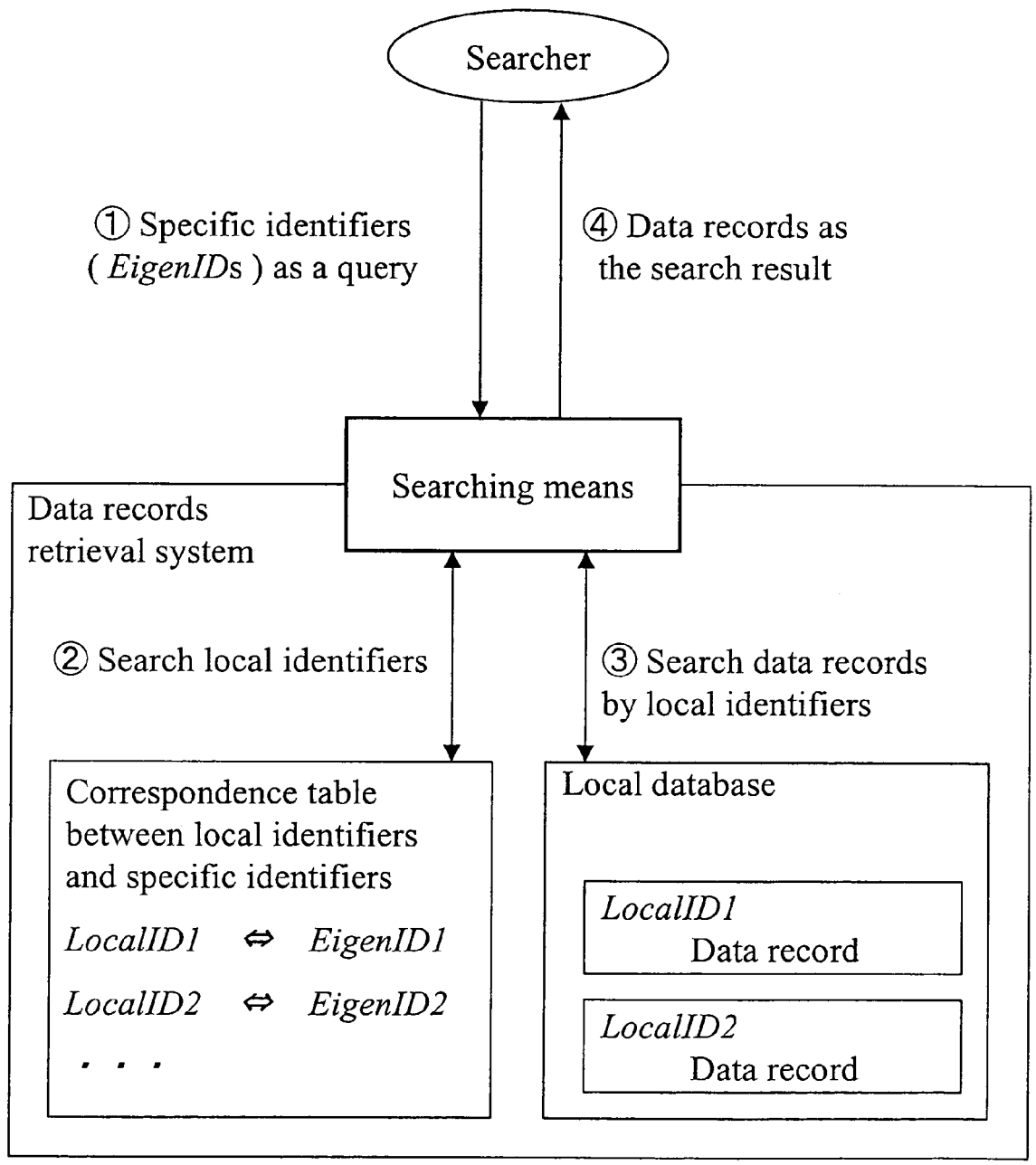
FIG. 12 shows an example of data records managed by local identifiers are searched by the specific identifiers of the sequence as a query.

A data retrieval system in which it is possible to search data records using specific identifiers of sequences of the present invention as queries is shown in FIG. 12.

In the system, local identifiers have been given to data records internally. The local identifiers of data records (LocalID1, LocalID2 etc. in FIG. 12) are used locally in the system. In the data retrieval system, there is a correspondence table associating specific identifiers of sequences with local identifiers. And the correspondence can be altered, added, or deleted by administrators of the system. Furthermore, in the system, there are one or more local databases managing data records with local identifiers, therefore, it is possible to search data records in the databases using local identifiers as queries by "searching means" of the system. "Searching means," "correspondence table of identifiers," and "local databases" may exist on a single computer or multiple computers among which the communication may be carried out via networks or the internet. Moreover, administrator of the correspondence table of identifiers and administrator of local databases may be different. Any means may be applicable for the correspondence table of identifiers as long as corresponding local identifiers can be searched from specific identifiers. The correspondence between specific identifiers and local identifiers are multiple-to-multiple correspondence.

The procedure for search is as follows;

A searcher who is outside of the "data retrieval system" transmits a search query including one or more specific identifiers of sequences to the "searching means" of the system (FIG. 12 ①) Firstly, "Searching means" searches local identifiers corresponding to the specific identifiers using the correspondence table of identifiers (FIG. 12 ②). And secondly, using the local identifiers, "searching means" searches data records in the local databases by using the local identifiers (FIG. 12 ③). Finally, "searching means" returns searched data records to the searcher. As other method, if the correspondence table of identifiers and table of data records in local databases are merged in advance utilizing a "view" function which is a function by relational databases, the search (② and ③) can be conducted collectively. By utilizing file systems as the local databases, the local identifiers may be the local file names.

In this example, the searcher is able to search data records by specific identifiers of the sequences only, furthermore, he is able to search data records with which the specific identifiers are associated by the correspondence table 'at the time of search.' (FIG. 12 ④) By alteration, addition, and deletion of correspondence in the correspondence table, the administrator of the system can always set the system to return appropriate data records to the searcher's requests at the time of search.

Moreover, in case that a data record with which a specific identifier was supposed to be associated does not exist in the local database due to alteration and deletion of data records, he can set the system to return correction information pertaining to the sequence instead of the data record. Furthermore, the searcher can search multiple databases at the same time by sending the same specific identifiers as a query to multiple database systems as shown in FIG. 12 via networks and the intranet. Owing to the present invention, the administrator of the system can generate globally specific identifiers to the sequences contained in data records of the system by themselves. And they are not dependent on a certain authority like GenBank. Owing to the invention, the searcher is able to generate, by himself, the specific identifiers of the sequences that he want to search.

Example 9

Figure 13:
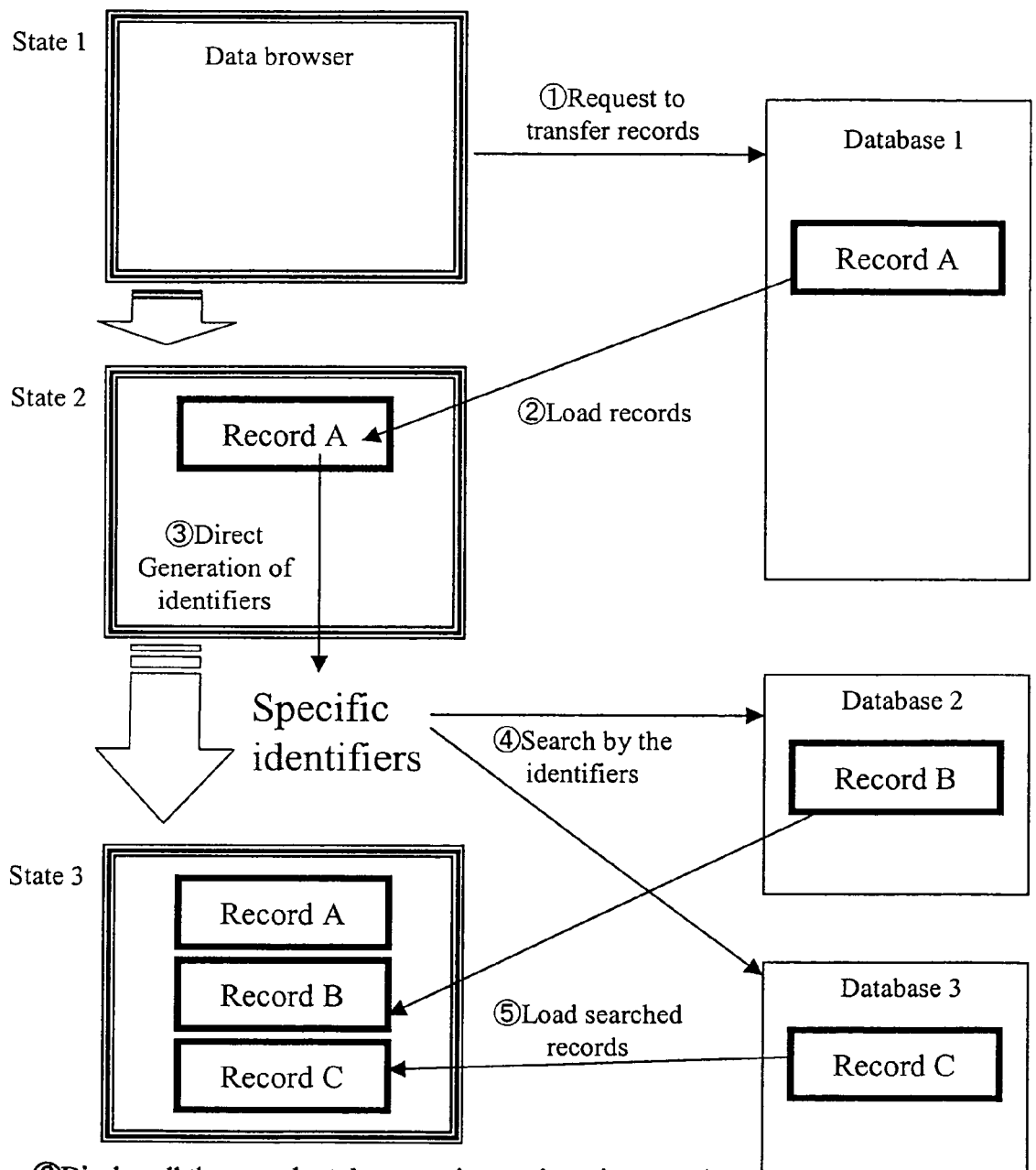
FIG. 13 shows an example of data browser automatically generating specific identifiers from data records loaded in the browser, searching databases and displaying the searched results for the user.

In FIG. 13, "Data browser" is an apparatus used to view data records through the networks or the internet. Database 1 is a data-record-service means which serves data records containing sequences, which can be located at any site, or can be located at any internet site, for example, NCBI, EBI or DDBJ where data records are released, or can be an inhouse server connected by the networks within a firewall. "Data browser" is equipped with "means of generating specific identifiers" and carries out the following procedures automatically.

① "Data browser" transmits the transfer request of data records to database 1, which may be via servers on the internet, ② Load the requested data records on the "data browser."

③ When a string of characters representing a base sequence and/or an amino-acid sequence in the loaded data records, the "data browser" directly generates a specific identifiers to the sequence based on the string of characters representing the sequence by the "means of generating specific identifiers." When information specifying the segment/segments of the sequence exists such as the regions at "FEATURE" section in files of base sequences in the GenBank, specific identifiers are further generated for that segment/segments of the sequence.

④ Automatically or after the approval of the user, the "data browser" searches data records with which the generated specific identifiers are associated in another database 2 by sending the specific identifiers as a query. Database 2 may exist within the apparatus where the data browser exists, or may exist on a different computer via network, or may exist on a computer on a remote site via the internet. Moreover, in addition to the database 2, the same search query may be transmitted to the other database 3 in parallel or sequentially. Number of databases is not limited here.

⑤ "Data browser" loads new data records as the search result.

⑥ "Data browser" displays information clearly to the users based on the loaded data in the data records. These data records may be integrated and displayed.

⑦ If specific identifiers of the present invention are included in the loaded data records in ⑤ or a string of characters representing a sequence exist or an information which specifies a segment/segments in addition to a string of characters representing a sequence exists, new specific identifiers are generated by the functions of the "data browser" similar to ③, and the procedures of ④, ⑤, and ⑥ can be repeated proper number of times. In case the procedures are repeated automatically, it is possible to carry out the procedure ⑥ only for the last time.

"Data browser" can be consisted of a computer and programs so written as to have the above-mentioned functions. Furthermore, universal internet browsers such as "Internet Explorer" and "Netscape Navigator" and proper additional means of the above-mentioned functions to the universal browsers may be used. It is possible to use software of certain models such as "Plugins," "Java applets" and "ActiveX components" as means of timely additions, however, other similar software may be applicable. It is also applicable to prepare a means for authentication of users and a means to select which databases are to be searched. Moreover, at any time via the networks, it is possible to update modules used for extraction of strings of characters representing sequences from data records so as to cope with the changes of formats of data records. Owing to this "data browser," even if specific identifiers are not included in the data record viewed, it is possible to "directly" generate specific identifiers (this is the definition of "direct generation of identifiers" in the present description). And it is possible to search other databases automatically using specific identifiers as a query, and to inform the obtained information to the users who are viewing the "data browser." When web pages of various internet sites serving data records containing sequences are browsed by the above-mentioned "data browser," it is possible to judge whether or not information related to sequences viewed exists in other databases by functions of above-mentioned "data browser." The "data browser" may have function of editing annotations and adding them to the databases. Moreover, the browser can be used as an apparatus to inform annotations related to the sequences or segment/segments of the sequences to the users, or an apparatus to obtain annotations from databases provided by "annotation-service providers" who provide annotation data. In addition to the user-authentication functions of the browser, those who provide annotation data can set servers providing data records to count the times of search so that they can charge according as the search.

INDUSTRIAL APPLICABILITY

By the method of the present invention, specific identifiers generated at different computers can be transmitted globally via the internet without causing any inconsistency. Data records containing sequences can be exchanged between remote databases via the internet without care about the name space of the identifiers. Database administrator do not have to retrieve global identifiers from authorities such as GenBank, and instead, are able to generate global identifiers by themselves. Specific identifiers are not always necessary to be included in the data records, because the identifiers can be "directly" generated from sequences contained in the data records if necessary. Thus, internet browser can generate specific identifiers of sequences and search additional information on the sequences by the identifiers, even when a data record viewed does not contain any identifiers. Annotations created at different web sites can be easily integrated and understandably viewed by only comparing specific identifiers, because the generated identifiers used to describe annotations at different sites are consistent globally. Only by comparison of the specific identifiers, it is possible to judge whether the information in different data records are related to the same sequence or not. Using the method of the present invention, specific identifiers can be generated from base sequences or amino-acid sequences with extremely low probability of collision of the identifiers. These identifiers can be generated extremely rapidly and easily from base sequences or amino-acid sequences wherever in the world. Moreover, since identifiers are specific and there is no possibility of collision substantially, it is possible to judge the identicalness of sequences easily by comparison of identifiers only.

---

The invention claimed is:

1. A method of generating an identifier specific to a base sequence or an amino-acid sequence or a segment/segments of a sequence comprising converting data with a conversion function to generate the identifier, wherein the data comprises a representation of connection order of residues in the sequence or the segment/segments of the sequence, and wherein the generated identifier is specific to the sequence and specific to descriptive information related to the sequence other than strings of characters representing the sequence of amino acids or nucleotides, and wherein the identifier is derived from the sequence itself.

2. The method of claim 1, in which the data representing connection order of the residues is transformed to a standard representation which is converted to the identifier, whereby the conversion function generates the same identifier regardless of the initial representation of the same sequence or the same segment/segments of the sequence.

3. The method of claim 1, wherein the conversion function comprises one or more collision-intractable hash functions and/or universal one-way hash functions.

4. The method of claim 1, wherein the conversion function comprises secure hash algorithm (SHA) or SHA1.

5. The method of claim 1, wherein the identifier is appended with one or more characters representing the generation method of the identifiers and/or additional information.

6. The method of claim 1, wherein the identifier has a fixed length.

7. A method of assigning the same identifier to the same sequence and/or to the same segment/segments of the sequence that occurs more than once among data records of one or more databases, comprising converting sequence data for each same sequence and/or to the same segment/segments with the same conversion function by a method of claim 1.

8. A method of generating an identifier of a group including multiple sequences and/or segment/segments of sequences, comprising generating an identifier for each member of the group by the method of claim 1, and generating an identifier specific to combination of the identifiers of the sequences and/or segment/segments of the sequences in the group.

9. A method of judging the identicalness of sequences, segment/segments of sequences, genotypes and/or alleles by comparing identifiers generated by the method of claim 1.

10. A method of searching a data record containing a sequence or segment/segments of a sequence or a genotype or an allele by directly generating an identifier from data representing connection order of residues by a method of claim 1, and by searching for one or more data records in one or more databases using the identifier.

11. The method of claim 1, comprising storing the identifier and/or one or more data records containing the identifier on a storage a device or a recording medium.

12. A storage device or a medium recording a program comprising the method of claim 1, and a device for generating an identifier according to the method of claim 1.

13. A method of generating an identifier of a data record containing a sequence or segment/segments of a sequence, wherein the identifier is generated from both the identifier generated by a method of claim 1 and information related to the sequence or segment/segments of the sequence in the data record, whereby the generated identifier is specific to combination of the sequence or segment/segments of the sequence and information related to the sequence of segment/segments of the sequence in the data record.

14. The method of claim 13 wherein the identifier is specific for a sequence and/or segment/segments of a sequence of a selected genotype or allele.

15. The method of claim 14, wherein the identifier describes a relation among sequences and/or segment/segments of sequences and/or genotypes and/or alleles.

16. The method of claim 14, wherein the identifier describes information related to sequences and/or segment/segments of sequences and/or genotypes and/or alleles.

17. The method of claim 14, wherein the identifier is compared with identifiers generated of one or more data records in one or more databases to identify the occurrence of the same identifier, or a part thereof.

18. The method of claim 14, wherein the identifier describes an association of an identifier with one or more data records in one or more databases.

19. The method of claim 18, wherein the data record does not include data representing connection order of residues in a sequence or segment/segments of the sequence.

* * * * *

UNITED STATES PATENT AND TRADEMARK OFFICE
CERTIFICATE OF CORRECTION

| | | |
|---|---|---|
| PATENT NO. | : 7,164,991 B1 | Page 1 of 1 |
| APPLICATION NO. | : 10/048479 | |
| DATED | : January 16, 2007 | |
| INVENTOR(S) | : T. Toyoda et al. | |

It is certified that error appears in the above-identified patent and that said Letters Patent is hereby corrected as shown below:

On the Title Page at Item (56), References Cited (Foreign Patent Documents), "WO9815212911/1998" should be -- WO98/5212911/1998 --.

At column 30, line 55, "on a storage a device" should be --on a storage device--.

Signed and Sealed this

Thirteenth Day of November, 2007

JON W. DUDAS
*Director of the United States Patent and Trademark Office*

SEQUENCE LISTING

```
<160> NUMBER OF SEQ ID NOS: 12

<210> SEQ ID NO 1
<211> LENGTH: 153
<212> TYPE: PRT
<213> ORGANISM: Human

<400> SEQUENCE: 1

Gly Leu Ser Asp Gly Glu Trp Gln Leu Val Leu Asn Val Trp Gly Lys
1               5                   10                  15

Val Glu Ala Asp Ile Pro Gly His Gly Gln Glu Val Leu Ile Arg Leu
            20                  25                  30

Phe Lys Gly His Pro Glu Thr Leu Glu Lys Phe Asp Lys Phe Lys His
        35                  40                  45

Leu Lys Ser Glu Asp Glu Met Lys Ala Ser Glu Asp Leu Lys Lys His
    50                  55                  60

Gly Ala Thr Val Leu Thr Ala Leu Gly Gly Ile Leu Lys Lys Lys Gly
65                  70                  75                  80

His His Glu Ala Glu Ile Lys Pro Leu Ala Gln Ser His Ala Thr Lys
                85                  90                  95

His Lys Ile Pro Val Lys Tyr Leu Glu Phe Ile Ser Glu Cys Ile Ile
            100                 105                 110

Gln Val Leu Gln Ser Lys His Pro Gly Asp Phe Gly Ala Asp Ala Gln
        115                 120                 125

Gly Ala Met Asn Lys Ala Leu Glu Leu Phe Arg Lys Asp Met Ala Ser
    130                 135                 140

Asn Tyr Lys Glu Leu Gly Phe Gln Gly
145                 150

<210> SEQ ID NO 2
<211> LENGTH: 153
<212> TYPE: PRT
<213> ORGANISM: Whale

<400> SEQUENCE: 2

Val Leu Ser Asp Ala Glu Trp Gln Leu Val Leu Asn Ile Trp Ala Lys
1               5                   10                  15

Val Glu Ala Asp Val Ala Gly His Gly Gln Asp Ile Leu Ile Arg Leu
            20                  25                  30

Phe Lys Gly His Pro Glu Thr Leu Glu Lys Phe Asp Lys Phe Lys His
```

```
                35                  40                  45
Leu Lys Thr Glu Ala Glu Met Lys Ala Ser Glu Asp Leu Lys Lys His
             50                  55                  60

Gly Asn Thr Val Leu Thr Ala Leu Gly Gly Ile Leu Lys Lys Lys Gly
 65                  70                  75                  80

His His Glu Ala Glu Leu Lys Pro Leu Ala Gln Ser His Ala Thr Lys
                 85                  90                  95

His Lys Ile Pro Ile Lys Tyr Leu Glu Phe Ile Ser Asp Ala Ile Ile
                100                 105                 110

His Val Leu His Ser Arg His Pro Gly Asp Phe Gly Ala Asp Ala Gln
                115                 120                 125

Ala Ala Met Asn Lys Ala Leu Glu Leu Phe Arg Lys Asp Ile Ala Ala
            130                 135                 140

Lys Tyr Lys Glu Leu Gly Phe Gln Gly
145                 150

<210> SEQ ID NO 3
<211> LENGTH: 153
<212> TYPE: PRT
<213> ORGANISM: Rat

<400> SEQUENCE: 3

Gly Leu Ser Asp Gly Glu Trp Gln Leu Val Leu Asn Val Trp Gly Lys
 1               5                  10                  15

Val Glu Gly Asp Leu Ala Gly His Gly Gln Glu Val Leu Ile Lys Leu
                20                  25                  30

Phe Lys Asn His Pro Glu Thr Leu Glu Lys Phe Asp Lys Phe Lys His
                35                  40                  45

Leu Lys Ser Glu Asp Glu Met Lys Gly Ser Glu Asp Leu Lys Lys His
             50                  55                  60

Gly Asn Thr Val Leu Thr Ala Leu Gly Gly Ile Leu Lys Lys Lys Gly
 65                  70                  75                  80

Gln His Ala Ala Glu Ile Gln Pro Leu Ala Gln Ser His Ala Thr Lys
                 85                  90                  95

His Lys Ile Pro Ile Lys Tyr Leu Glu Phe Ile Ser Glu Ala Ile Ile
                100                 105                 110

Gln Val Leu Gln Ser Lys His Pro Gly Asp Phe Gly Ala Asp Ala Gln
                115                 120                 125

Gly Ala Met Ser Lys Ala Leu Glu Leu Phe Arg Asn Asp Ile Ala Ala
            130                 135                 140

Lys Tyr Lys Glu Leu Gly Phe Gln Gly
145                 150

<210> SEQ ID NO 4
<211> LENGTH: 26
<212> TYPE: PRT
<213> ORGANISM: Artificial Sequence
<220> FEATURE:
<223> OTHER INFORMATION: Made up sequence for example of method
<220> FEATURE:
<221> NAME/KEY: X
<222> LOCATION: (19)..(23)
<223> OTHER INFORMATION: Any amino acid

<400> SEQUENCE: 4

Glu Asp Leu Gln Gly Asp Ala Val Pro Glu Thr Ser Ala Thr Lys Asp
 1               5                  10                  15

Asp Asn Glu Xaa Pro Glu Met Ile Pro Met
```

```
                        20                  25

<210> SEQ ID NO 5
<211> LENGTH: 26
<212> TYPE: PRT
<213> ORGANISM: Artificial Sequence
<220> FEATURE:
<223> OTHER INFORMATION: Made up sequence for example of method

<400> SEQUENCE: 5

Asp Asp Leu Gln Gly Thr Ala Val Gln Glu Arg Ser Ala Lys Ala Ser
1               5                  10                  15

Asp Glu Glu Glu Ala Ile Arg Thr Leu Leu
            20                  25

<210> SEQ ID NO 6
<211> LENGTH: 17
<212> TYPE: PRT
<213> ORGANISM: Artificial Sequence
<220> FEATURE:
<223> OTHER INFORMATION: Made up sequence for example of method

<400> SEQUENCE: 6

Met Lys Leu Ser Ile Thr Glu Trp Pro Gln Asn Met Cys Ser Ala Leu
1               5                  10                  15

Arg

<210> SEQ ID NO 7
<211> LENGTH: 12
<212> TYPE: PRT
<213> ORGANISM: Artificial Sequence
<220> FEATURE:
<223> OTHER INFORMATION: Made up sequence for example of method

<400> SEQUENCE: 7

Lys Pro Val Ser Leu Ser Tyr Arg Cys Pro Cys Arg
1               5                  10

<210> SEQ ID NO 8
<211> LENGTH: 27
<212> TYPE: PRT
<213> ORGANISM: Artificial Sequence
<220> FEATURE:
<223> OTHER INFORMATION: Made up sequence for example of method

<400> SEQUENCE: 8

Lys Pro Val Ser Leu Ser Tyr Arg Cys Pro Cys Arg Phe Phe Glu Glu
1               5                  10                  15

Ser His Asn Pro Gln Glu Ala Ser Val Asn Met
            20                  25

<210> SEQ ID NO 9
<211> LENGTH: 8
<212> TYPE: PRT
<213> ORGANISM: Artificial Sequence
<220> FEATURE:
<223> OTHER INFORMATION: Made up sequence for example of method

<400> SEQUENCE: 9

Lys Trp Ile Gln Glu Tyr Glu Lys
1               5

<210> SEQ ID NO 10
<211> LENGTH: 30
<212> TYPE: DNA
```

-continued

```
<213> ORGANISM: Artificial Sequence
<220> FEATURE:
<223> OTHER INFORMATION: Made up sequence for example of method

<400> SEQUENCE: 10
atacgtagtg atgctgagtc gcgtagagtc                                    30

<210> SEQ ID NO 11
<211> LENGTH: 29
<212> TYPE: DNA
<213> ORGANISM: Artificial Sequence
<220> FEATURE:
<223> OTHER INFORMATION: Made up sequence for example of method

<400> SEQUENCE: 11
tgacgtagct gacgtcgacg tcgactgct                                     29

<210> SEQ ID NO 12
<211> LENGTH: 28
<212> TYPE: DNA
<213> ORGANISM: Artificial Sequence
<220> FEATURE:
<223> OTHER INFORMATION: Made up sequenc for example of method

<400> SEQUENCE: 12
cgctgagtcg atcgtcgact gacgctga                                      28
```